(12) United States Patent
Zhu et al.

(10) Patent No.: US 7,038,111 B2
(45) Date of Patent: May 2, 2006

(54) METHOD FOR INCREASING STRESS TOLERANCE IN PLANTS

(75) Inventors: Jian-Kang Zhu, Tucson, AZ (US); Liming Xiong, St. Louis, MO (US)

(73) Assignee: The Arizona Board of Regents, Tuscon, AZ (US)

( * ) Notice: Subject to any disclaimer, the term of this patent is extended or adjusted under 35 U.S.C. 154(b) by 425 days.

(21) Appl. No.: 10/231,035

(22) Filed: Aug. 30, 2002

(65) Prior Publication Data

US 2003/0084485 A1    May 1, 2003

Related U.S. Application Data

(60) Provisional application No. 60/317,724, filed on Sep. 6, 2001.

(51) Int. Cl.
*C12N 15/82* (2006.01)
*C12N 15/90* (2006.01)
*C12N 5/10* (2006.01)
*C12N 15/63* (2006.01)
*A01H 5/00* (2006.01)

(52) U.S. Cl. .................. 800/289; 435/419; 435/468
(58) Field of Classification Search ............. 435/320.1, 435/419, 468; 800/278, 289
See application file for complete search history.

(56) References Cited

OTHER PUBLICATIONS

Liming Xiong et al., The Arabidopsis LOS5/ABA3 Locus Encoes a Molybdenum Cofactor Sulfurase and Modulates Cold Stress- and Osmotic Stress-Responsive Gene Expression, The Plant Cell, vol. 13, 2063-2083, Sep. 2001.
Bittner et al., Identification and characterization of the Arabidopsis thaliana molybdenum cofactor sulfurase, Dec. 1, 2000, GenBank Acc. No. Af325457.
Adams et al., The genome sequence of Drosophila melanogaster, Mar. 21, 2000, GenBank Acc. No. AAFS0901.
Amrani et al., Comparison of the sequences of the Aspergillus nidulans hxB and Drosophila melanogaster ma-1 genes with nifS from Azotobacter vinelandii suggests a mechanism for the insertion of the terminal sulpnur atom in the molybdopterin cofactor, Feb. 12, 1999, GenBank Acc. No. AAF22564.
L. Xiong et al., The Arabidopsis LOS5/ABA3 locus encodes a molybdenum cofactor sulfurase and modulates cold stress- and osmotic stress-responsive gene expression, May 15, 2001, GenBank Acc. No. AYO34895.
Karimi, et al., Gateway™ vectors for Agrobacterium-mediated plant transformation, Published online: Apr. 11, 2002, Trends in Plant Science, vol. 7, No. 5 May 2002.
U.S. Appl. No. 09/824,734, filed Apr. 4, 2001, Zhu et al.
U.S. Appl. No. 09/824,735, filed Apr. 4, 2001, Zhu et al.
U.S. Appl. No. 10/231,035, filed Aug. 30, 2002, Zhu et al.
M. Sagi, et al., Physiologia Plantarum, vol. 99, pp. 546-553, "Nitrate Reductase and Molybdenum Cofactor in Annual Ryegrass as Affected by Salinity and Nitrogen Source", 1997.
M. Sagi, et al., The Plant Journal, vol. 31, pp. 305-317, "The Absence of Molybdenum Cofactor Sulfuration is the Primary Cause of the Flacca Phenotype in Tomato Plants", 2002.
R. R. Mendel, et al., Journal of Experimental Botany, vol. 53, No. 375, pp. 1689-1698, "Molybdoenzymes and Molybdenum Cofactor in Plants", Aug. 2002.
F. Bittner, et al., The Journal of Biological Chemistry, vol.276, No. 44, pp. 40381-40384, "ABA4 is a Molybdenum Cofactor Sulfurase Required for Activation of Aldehyde Oxidase and Xanthine Dehydrogenase in Arabidopsis Thaliana", Nov. 2001.

*Primary Examiner*—Ashwin Mehta
(74) *Attorney, Agent, or Firm*—Oblon, Spivak, McClelland, Maier & Neustadt, P.C.

(57) ABSTRACT

The present invention provides methods and compositions for improving the drought resistance of plants. More specifically, the present invention utilizes overexpression of a molybdenum cofactor sulfurase in plants and plant cells.

43 Claims, 12 Drawing Sheets

Figure 8

```
   1 atggaagcat ttcttaagga attcggagat tattatggat acccagatgg tcccaagaac
  61 attcaagaga tccgcgacac cgaattcaag agattagata aaggtgttgt atacttggat
 121 catgctggtt ctactttgta ttctgagttg cagatggaat atatttttaa ggacttcaca
 181 agcaatgttt ttggaaatcc acatagtcaa agtgatatca gttcggccac cagtgacctt
 241 atagcggatg ctcgacatca ggtgcttgaa tactttaatg catctcctga agattacagt
 301 tgcttattca cctccggagc cacagcagcg ctgaagcttg tcggagagac ttttccgtgg
 361 acccaagaca gtaatttttt gtataccatg gagaatcaca acagtgtact tggtattagg
 421 gaatatgcat tagctcaagg tgcttcagca tgtgcagtgg atattgaaga ggcagctaac
 481 caaccaggcc agcttacaaa ttcaggacca tctatcaagg taaagcatcg tgctgtgcag
 541 atgagaaaca cttctaaact ccaaaaggaa gagtcaagag gaaatgccta taatctattt
 601 gctttcccct cggagtgcaa ttttctggc ctgaggttta atctagatct ggtgaagttg
 661 atgaaagaaa atactgagac cgtgctacaa ggctccccct ttagcaagag caagcggtgg
 721 atggtcttga ttgatgctgc aaagggttgt gctacactac cacctgattt atcggagtat
 781 cctgcagatt ttgttgttct gtcattctac aagttatttg gttatcctac tgggcttggc
 841 gctctccttg tacggaatga tgcagccaaa ttgctcaaaa agacttattt tagtggaggc
 901 actgttgctg cttcaattgc tgacatcgac tttgtaaaaa gaagggaaag ggtggaggag
 961 tttttgagg atggttctgc ttcattcctg agcatagcag ccatccgtca tggcttcaaa
1021 ttactcaagt cgcttacacc ttctgcaatt tggatgcaca caacgtcact ttccatatat
1081 gtgaaaaaga agcttcaggc tttacgacat ggaaacgggg ctgctgtatg tgttctgtat
1141 ggcagtgaaa atctggagtt atcttcacat aaatcaggcc caacggttac attcaacttg
1201 aaaagacctg atggctcttg gtttggctac ttggaggtgg agaagcttgc ttctttatct
1261 ggaattcagt tacggacagg atgttttgc aatcctggcg catgtgcaaa gtatctcgag
1321 ttatcccatt ctgagctacg gtctaatgta gaggctgggc atatttgctg ggatgacaat
1381 gatgtgataa atggaaaacc aacagggct gttagggttt cgtttggtta tatgtcaacc
1441 tttgaagatg ccaagaaatt tattgatttc atcataagtt catttgcttc acctccaaag
1501 aagactggga atggaaccgt cgtcagtgga aggtttcctc aacttcctag tgaagacctt
1561 gaaagtaaag aatctttttcc aagccactac cttaagtcaa ttactgtata cccgatcaag
1621 tcatgtgctg gatttctgt gatacgttgg ccactttgca gaacaggcct gctgcatgat
1681 cgagaatgga tggttcaggg tctgaccggt gaaattctta cccaaaagaa ggtgcctgag
1741 atgtctctta taaaaacctt tatcgacctt gaggaaggac tactgtctgt agaatcttct
1801 cgctgcgaag acaagttgca catcagaatc aagtctgatt catataaccc gaggaacgat
1861 gagtttgatt cacatgccaa catacttgaa aaccgtaatg aggaaactag aatcaatcgt
1921 tggttcacca atgccattgg tcgacaatgc aagttgctac ggtattctag ctctacttcc
1981 aaagactgct tgaacagaaa caagagtcct ggtttgtgca gagatttgga aagcaatatc
2041 aactttgcta atgaagctca gttcttgtta atctccgagg agagtgttgc tgacctaaac
2101 agaagattag aagcaaaaga cgaggattac aaacgggctc atgaaaaact caatccacat
2161 aggttcagac caaatctggt tatatctgga ggtgaaccat acggggaaga taaatggaaa
2221 actgtcaaga taggagacaa tcatttcaca tcattgggcg gttgtaaccg gtgccagatg
2281 ataaacataa gtaatgaagc tggactagtg aagaaatcca atgagccctt aacaacttta
2341 gcttcatata ggagagtaaa gggaaagatc ttgtttggaa cgcttttgag atacgagatt
2401 gatgagaaaa gacaatgttg gattggagtt ggggaagaag ttaatccaga tattgaataa
```

Figure 9

METHOD FOR INCREASING STRESS TOLERANCE IN PLANTS

CROSS-REFERENCE TO RELATED APPLICATIONS

This application claims benefit to U.S. Provisional Application Ser. No. 60/317,724, filed on Sep. 6, 2001, incorporated herein by reference in its entirety.

STATEMENT OF GOVERNMENTAL SPONSORSHIP

The invention described herein was supported by NSF grants IBN-9808398 and DBI-9813360. The government may have certain rights in this invention.

BACKGROUND OF THE INVENTION

1. Field of the Invention

The present invention relates to methods and compositions for increasing stress tolerance in plants. More specifically, the present invention provides methods and compositions for improving drought resistance, salt tolerance, and resistance to freezing.

2. Background of the Invention

Plants respond to environmental challenges in part by altering their gene expression profile that ultimately leads to various adaptive responses at cellular and whole plant levels (Bray, 1993; Thomashow, 1999; Hasegawa et al., 2000; Zhu et al., 1997; Ingram and Bartel, 1996). One important regulator of plant responses to abiotic stress environments is the phytohormone abscisic acid (ABA). ABA is involved in plant responses to abiotic stress such as low temperature, drought, and salinity, as well as the regulation of plant growth and development including embryogenesis, seed dormancy, shoot and root growth and leaf transpiration (Koornneef et al., 1998; McCourt, 1999; Leung and Giraudat, 1998; Rock, 2000). Evidence for a role of ABA in stress-responsive gene regulation in plants has been two-fold. Firstly, under cold, drought, or salt stress conditions, plants accumulate increased amount of ABA, with drought stress having the most prominent effect on ABA accumulation. Secondly, the expression of many stress-responsive genes is induced by exogenous ABA, and their stress-inducibility is decreased in mutant plants defective in ABA biosynthesis or responsiveness.

Genetic analysis based on the inhibitory effect of ABA on seed germination has yielded mutants with reduced ABA biosynthesis or altered ABA responsiveness (Koornneef et al., 1998; McCourt, 1999; Leung and Giraudat, 1998; Rock, 2000). The former group of mutants in Arabidopsis includes aba1, aba2, and aba3. The ABA1 gene encodes a zeaxanthin epoxidase that functions in an early step of ABA biosynthesis by converting zeaxanthin to violaxathin. Molecular cloning of ABA2 or ABA3 has not been reported thus far. Common phenotypes of these aba mutants include loss in seed dormancy, germination resistance to NaCl stress, and withering when transferred from high humidity to low humidity conditions. The utilization of ABA deficient mutants along with ABA response mutants in stress gene regulation studies led to the notion that stress-responsive gene expression in plants is mediated by both ABA-dependent and ABA-independent pathways (Shinozaki and Yamaguchi-Shinozaki, 1997; Leung and Giraudat, 1998; Rock, 2000; Thomashow, 1999). Although the molecular mechanisms underlying the differences between ABA-dependent and ABA-independent gene regulation is unclear, analysis of the promoters of stress-responsive genes and the isolation of transcription factors that activate these genes support that there are distinct regulatory mechanisms for the different pathways. The ABRE (ABA-responsive element) complex in these promoters mediates gene induction by ABA (Guiltinan et al., 1990; Yamaguchi-Shinazaki and Shinozaki, 1994; Shen and Ho, 1995; Vasil et al., 1995), whereas the DRE/CRT (dehydration-responsive element) mediates cold and osmotic stress responsiveness independently of ABA (Yamaguchi-Shinozaki and Shinozaki, 1994; Stockinger et al., 1997). Despite these differences in transcriptional activation, genetic analysis has indicated that the ABA-dependent and ABA-independent pathways have extensive interactions or crosstalk in controlling gene expression under abiotic stresses (Ishitani et al., 1997; Xiong et al., 1999a).

As is well-appreciated in the field, there remains a need for methods of improving the resistance of plants to drought.

SUMMARY OF THE INVENTION

It is an object of the present invention to provide methods and compositions for increasing stress tolerance in plants.

It is another object of the present invention to provide plants and plant cells which have increased stress resistance.

The objects of the present invention, and others, may be accomplished with a method of increasing stress resistance in a plant, comprising overexpressing a molybdenum cofactor sulfurase in the plant.

The objects of the present invention may also be accomplished with a method of increasing stress resistance in a plant cell, comprising overexpressing a molybdenum cofactor sulfurase in the plant cell.

The objects of the present invention may also be accomplished with a plant or a plant cell transformed with a nucleic acid which encodes a molybdenum cofactor sulfurase.

Thus, the present invention also provides a method of producing such a plant or plant cell, by transforming a plant or plant cell with the nucleic acid which encodes the molybdenum cofactor sulfurase.

The present invention also provides an isolated and purified molybdenum cofactor sulfurase having the amino acid sequence of SEQ ID NO: 2.

The present invention also provides a method of producing the molybdenum cofactor sulfurase described above, comprising culturing host cells which have been transformed with a nucleic acid encoding the molybdenum cofactor sulfurase under conditions in which the molybdenum cofactor sulfurase is expressed, and isolating the molybdenum cofactor sulfurase.

In another embodiment, the present invention provides an isolated and purified enzyme having molybdenum cofactor sulfurase activity, wherein the amino acid sequence of the enzyme has a homology of from 70% to less than 100% to SEQ ID NO: 2

The present invention also provides a method of producing the enzyme described above, comprising culturing host cells which have been transformed with a nucleic acid encoding the enzyme under conditions in which the enzyme is expressed, and isolating the enzyme.

The present invention has been accomplished using a reporter gene approach to genetically dissect ABA and stress signal transduction in Arabidopsis. ABA and stress responsive bioluminescent plants were constructed by introducing the firefly luciferase reporter gene under control of the RD29A promoter (containing both ABRE and DRE/CRT elements; Yamaguchi-Shinozaki and Shinozaki, 1994) into Arabidopsis. The RD29A-LUC plants were mutagenized, and mutants with abnormal bioluminescence in response to cold, drought, salt or ABA were isolated (Ishitani et al., 1997). One group of mutants exhibit reduced luminescence responses to NaCl stress. Here, we present the characterization and cloning of two allelic mutants from this group. These two mutants, designated los5-1 and los5-2 (low expression of osmotically responsive genes), show reduced expression of stress-responsive genes under both cold and osmotic stress conditions. While the role of LOS5 in osmotic stress regulation of gene expression is mediated by ABA, the regulation of cold responsiveness by LOS5 is not dependent on ABA. The function of LOS5 in cold and osmotic stress responsive gene expression is independent of CBF/DREB1 or DREB2A transcription factors. los5 mutant plants are more susceptible to damage by freezing, salt and drought stresses, suggesting that LOS5 is critical for plant stress tolerance. The mutant plants also show enhanced transpirational water loss and accumulate less ABA in response to drought stress. Allelic tests show that los5 is allelic to the aba3 mutation. Map-based cloning of LOS5/ABA3 reveals that it encodes a putative molybdenum cofactor (MoCo) sulfurase that catalyzes the sulfuration of the desulfo form of MoCo, which is consistent with previous findings that the aba3 lesion is in the introduction of S into MoCo (Schwartz et al., 1997a). Sulfurylated MoCo is a cofactor of ABA-aldehyde oxidase that functions in the last step of ABA biosynthesis. Expression of the LOS5/ABA3 gene is up-regulated by ABA, salt and drought stresses. These data provide important insights into ABA biosynthesis and significantly further an understanding of stress gene regulation and stress tolerance.

A more complete appreciation of the invention and many of the attendant advantages thereof will be readily obtained as the same becomes better understood by reference to the following Figures in conjunction with the detailed description below.

The color scale at right shows the luminescence intensity from dark blue (lowest) to white (highest). Data in (G) to (I) represent means and standard errors (n=20). Open symbols, wild type; black symbols, los5-1.

Figure 2:
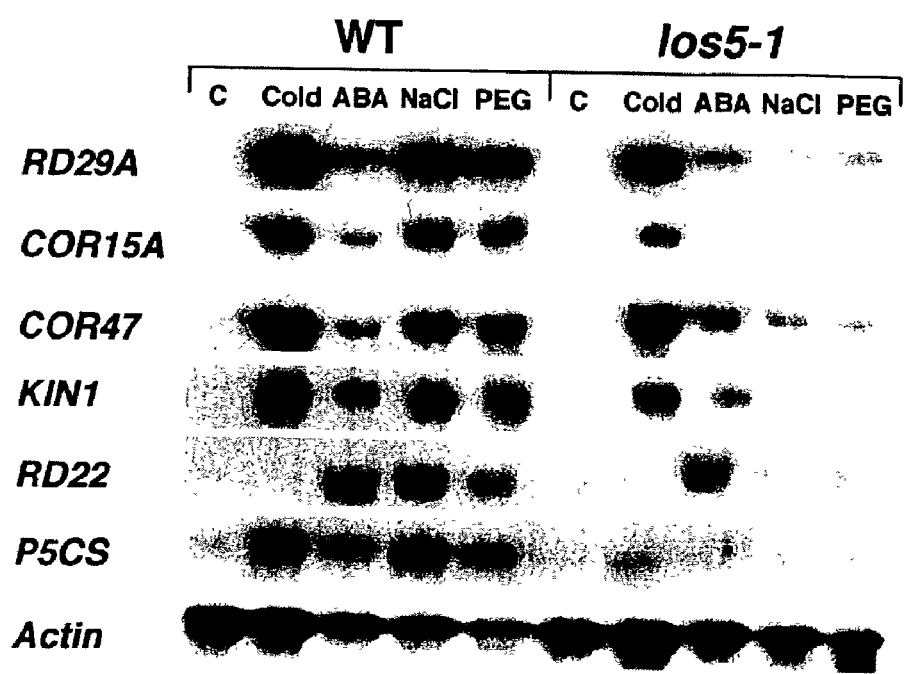

FIG. 2: Transcript levels of stress-responsive genes in los5-1 and wild-type plants. Seedlings were either not treated (control, C), or treated with low temperature (Cold, 0° C. for 24 hr), 100 μM ABA for 2 hr, 300 mM NaCl for 3 hr, or 30% PEG for 5 hr. Actin was used as a loading control. WT, wild type.

Figure 3:
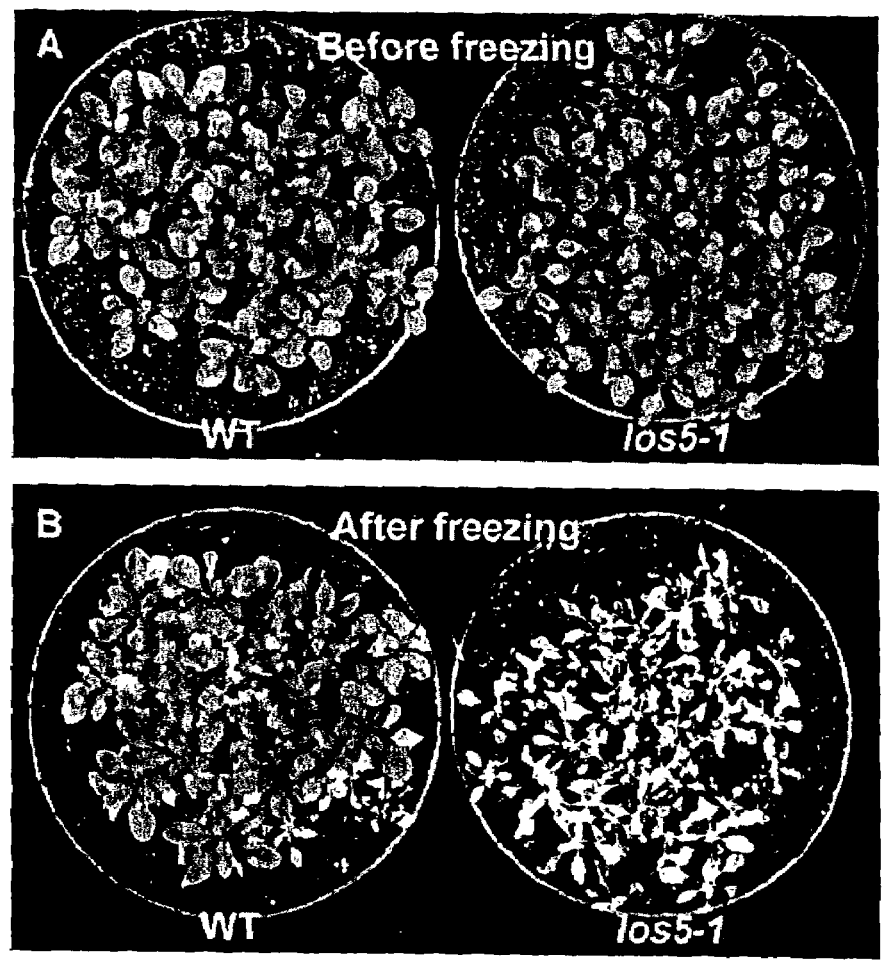

FIG. 3: Freezing sensitivity of los5-1 plants.
(A) Plants before freezing treatment.
(B) Plants after freezing treatment (−7° C. for 5 hr). The picture was taken 7 days after freezing treatment.

Figure 4:
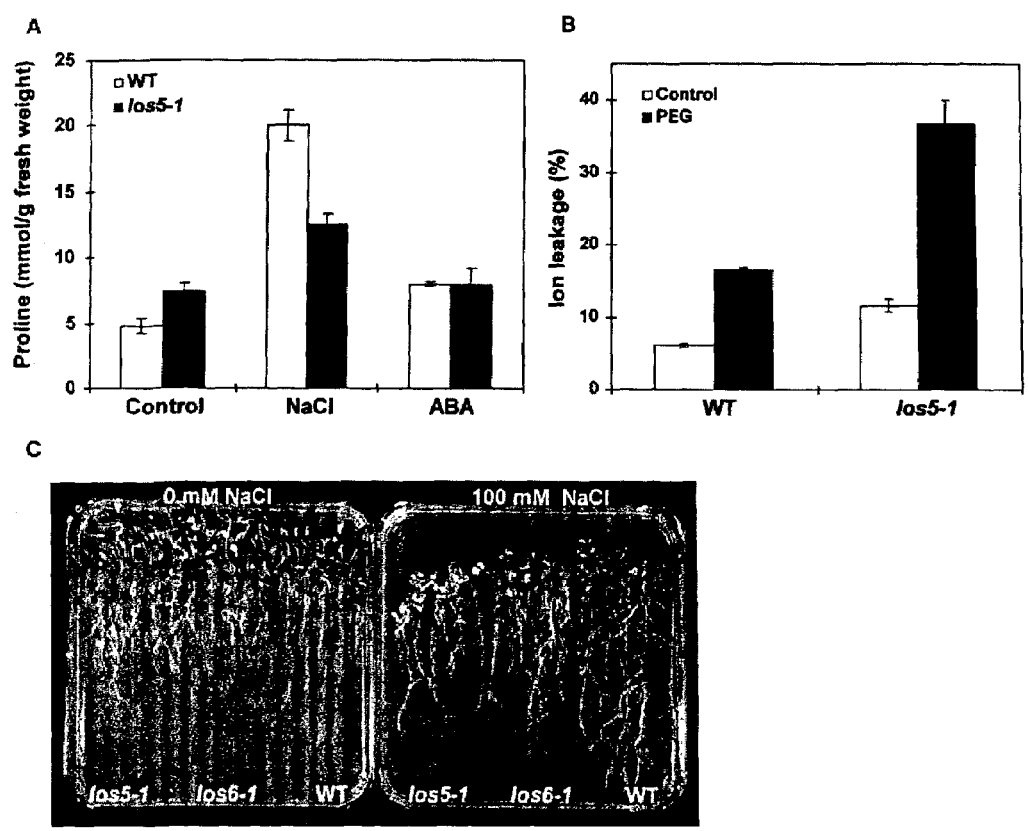

FIG. 4: Proline accumulation, and osmotic stress sensitivity of los5-1 mutant plants.
(A) Proline accumulation in los5-1 and wild type plants that were untreated (control), or 150 mM NaCl treated, or 50 μM ABA-treated. Data represent means and standard error (n=3).
(B) Drought sensitivity as measured by electrolyte leakage in wild type and los5-1 plants treated with 30% PEG. Data represent means and standard error (n=4).
(C) los5-1 plants are more sensitive to NaCl stress. One-week-old los5-1, los6/aba1, and wild type seedlings were transferred from MS nutrient agar medium to MS agar plate without NaCl (0 mM NaCl) or with 100 mM NaCl. Note that los5-1 mutant leaves were bleached due to NaCl stress. The pictures were taken 3 weeks after the seedlings were transferred to the treatment plates.

Figure 5:
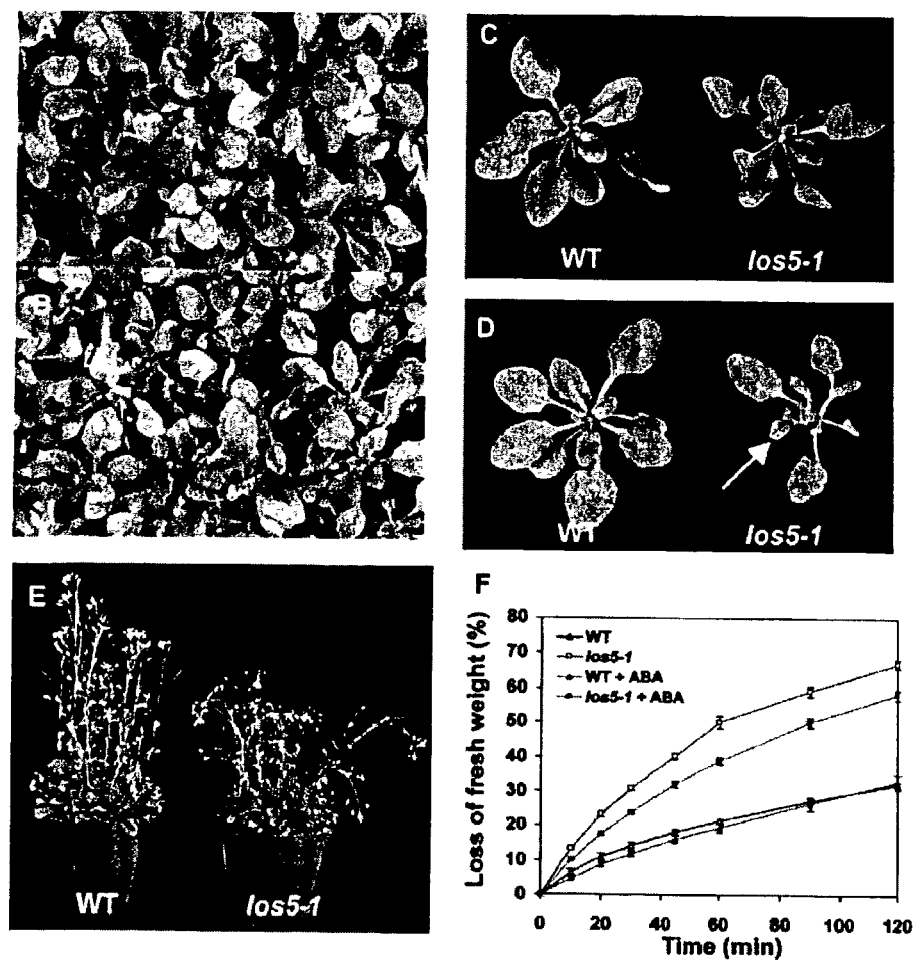

FIG. 5: Leaf morphology and wilty phenotypes of los5-1 mutant plants.
(A) Wild type plants in soil.
(B) los5-1 mutant plants in soil.
(C) Wild type and los5-1 rosette plants are turgid immediately after root detachment.
(D) los5-1 plants are wilty 10 min after root detachment. Arrow points to a wilty leaf in los5-1.
(E) Morphology of wild type (left) and los5-1 inflorescence 10 min after being moved from 90% relative humidity to ~30% relative humidity. Note los5-1 plants are wilty.
(F) Accumulative transpirational water loss in detached los5-1 and wild type shoots with or without 100 μM ABA treatment. Data are means and standard error (n=4).

Figure 6:
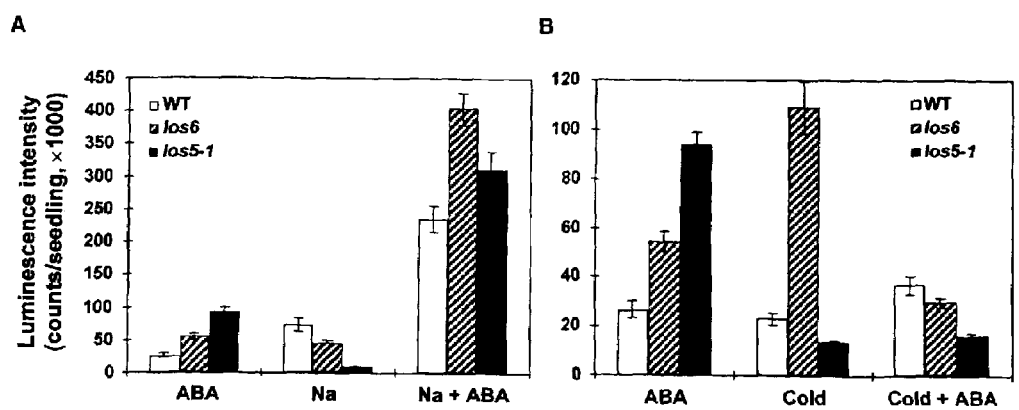

FIG. 6: Cold- or salt stress-regulation of RD29A-LUC expression in wild type, los5-1 and los6/aba1 seedlings as affected by exogenous ABA.
(A) Salt stress responsiveness in los5-1 and los6-1 mutants is rescued by ABA application.
(B) Cold responsiveness in los5-1 mutant is not rescued by ABA application. Data are means and standard errors (n—20). Cold, 0° C. for 48 hr; ABA, 100 μM for 4 hr; and Na, 300 mM NaCl for 4 hr.

Figure 7:
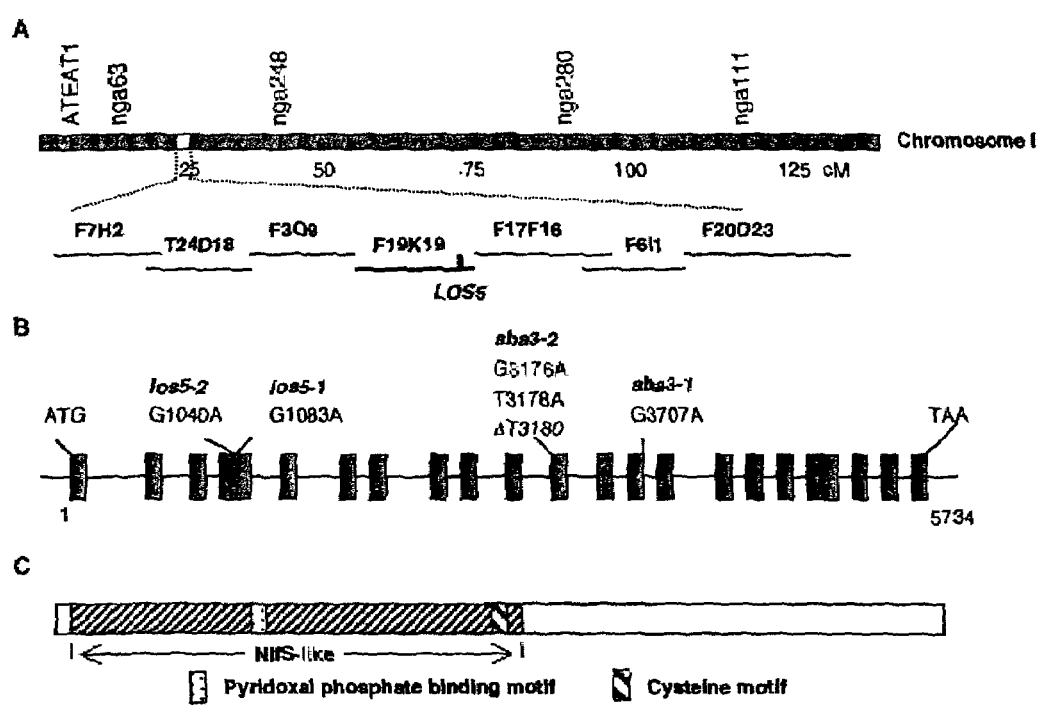

FIG. 7: Positional cloning of LOS5 and the organization of LOS5 gene and gene product.
(A) LOS5 was mapped to the upper arm of chromosome I and located on the BAC clone F19K19.
(B) Structure of the LOS5 gene and position of los5/aba3 mutations. Positions are relative to the translation initiation codon. Filled boxes indicate the open reading frame and lines between boxes indicate introns.
(C) Overall structure of LOS5 protein.

FIG. 8: Sequence of the cDNA sequence encoding the LOS5 protein (SEQ ID NO: 1).

Figure 9:
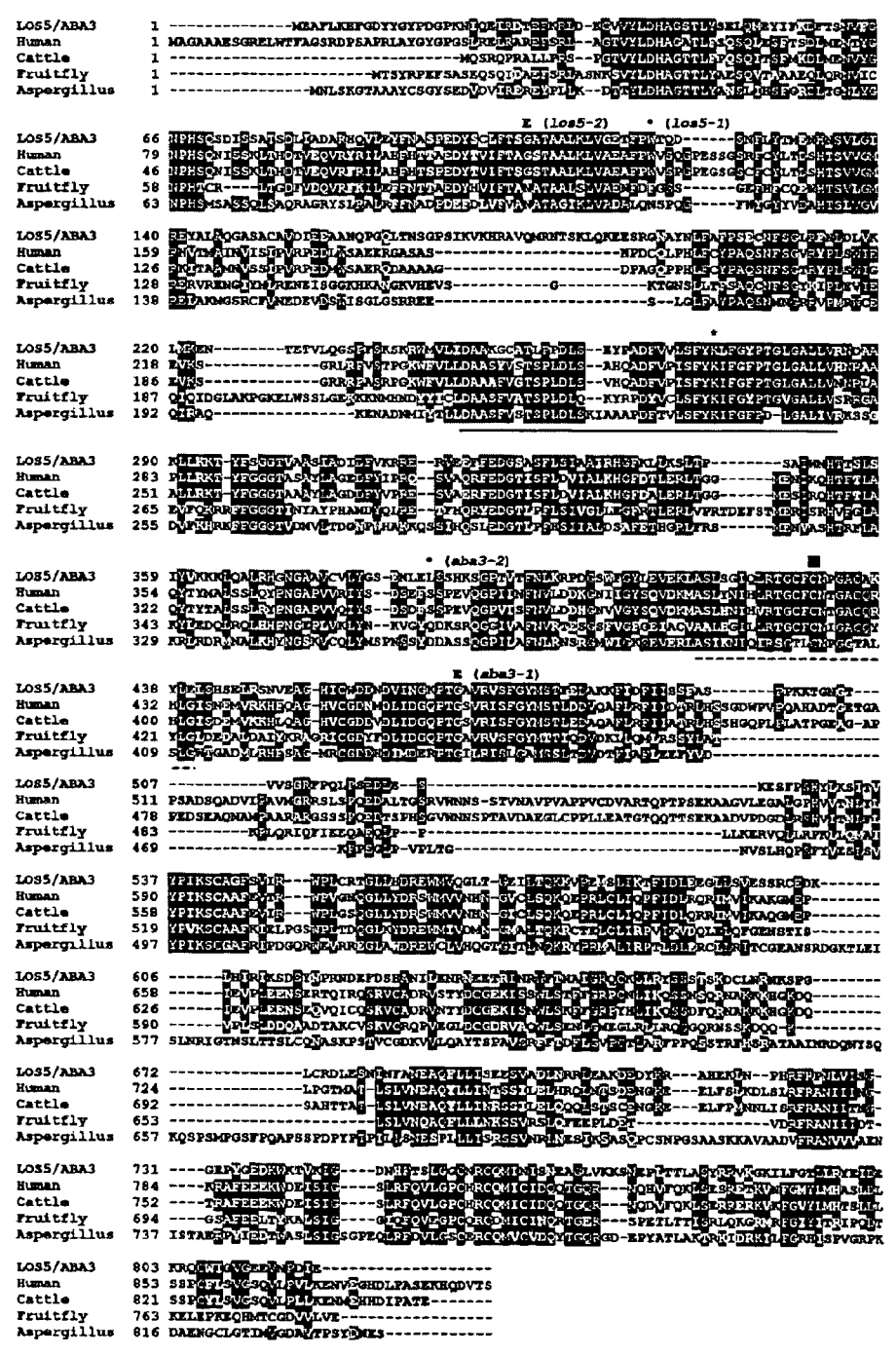

FIG. 9: Sequence alignment of LOS5 and its homologs from other organisms. Residues in black shade indicate identity and gray shade indicates similarity. Dotted lines indicate gaps that introduced to maximize alignment. The putative pyridoxal phosphate-binding motif is solid-underlined and the conserved cysteine motif is dash-underlined. The conserved critical lysine residue in the PLP domain is indicated with an asterisk, and the conserved cysteine residue is indicated with a square. Also shown are the positions of los5/aba3 mutations (filled circles indicate introduced stop codon). Sequence accession numbers for LOS5/ABA3 and its homologs are as follows: LOS5/ABA3, AY034895 (SEQ ID NO: 2); Human, BAA91354 (SEQ ID NO: 3); Fruitfly (Mal protein of *Drosophila melanogaster;* SEQ ID NO: 5), AAF50901; cattle (MCSU of *Bos Taurus;* SEQ ID NO: 4), BAA98133; and *Aspergillus* (HxB of *Aspergillus nidulans;* SEQ ID NO: 6), AAF22564.

Figure 10:
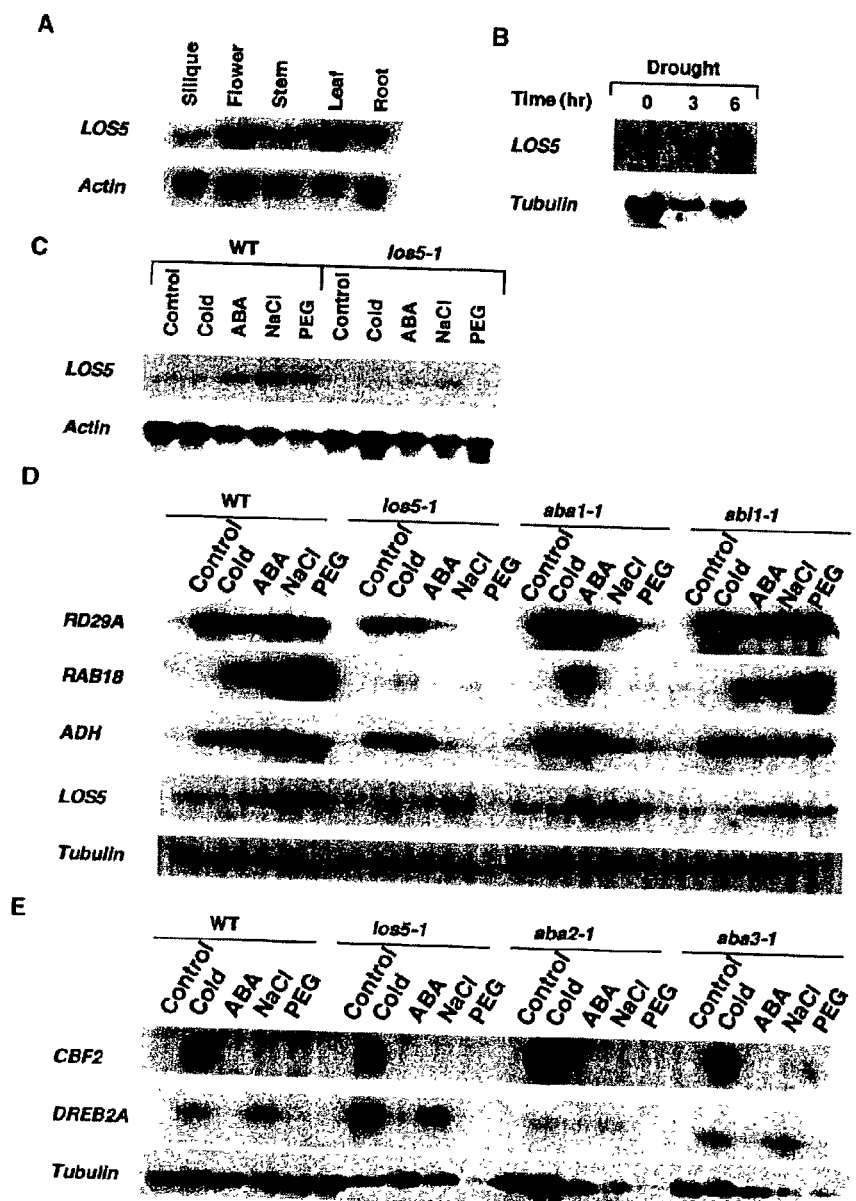

FIG. 10: LOS5/ABA3 gene expression and stress gene regulation in ABA deficient or insensitive mutants.

(A) LOS5 expression in different parts of plants.

(B) Up-regulation of LOS5 expression by drought in wild type seedlings.

(C) LOS5 expression under different stress treatments in wild type and los5-1 plants.

(D) Expression of LOS5 and selected other stress-responsive genes in los5-1, aba1-1, and abi1-1 plants.

(E) CBF2 and DREB2A expression in ABA-deficient mutants.

Control, untreated; cold, 4° C. for 12 hr; ABA, 100 μM ABA for 4 hr; NaCl, 300 mM NaCl for 5 hr; PEG, 30% PEG for 5 hr. Tubulin and actin are shown as loading controls.

Figure 11:
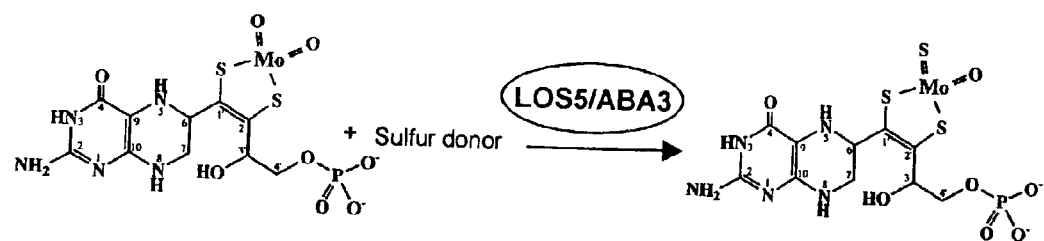

FIG. 11: Reaction catalyzed by LOS5/ABA3.

Desulfo/dioxyo form of molybdenum cofactor (MoCo) (left) needs to be sulfurylated at one of the two terminal oxyo groups by LOS5/ABA3 molybdenum cofactor sulfurase to generate the sulfide form of MoCo (right). The sulfide form MoCo is a cofactor of aldehyde oxidase (AO) and xanthine dehydrogenase (XDH), whereas the dioxyo form of MoCo is the cofactor for nitrate reductase (NR) and sulfite oxidase (SOX). AO catalyzes the last step of ABA biosynthesis. The immediate sulfur donor could be a cysteine residue, originated from LOS5/ABA3 or other sources. The structure of pterin and its numbering scheme are according to Rajagoplant (1991).

Figure 12:
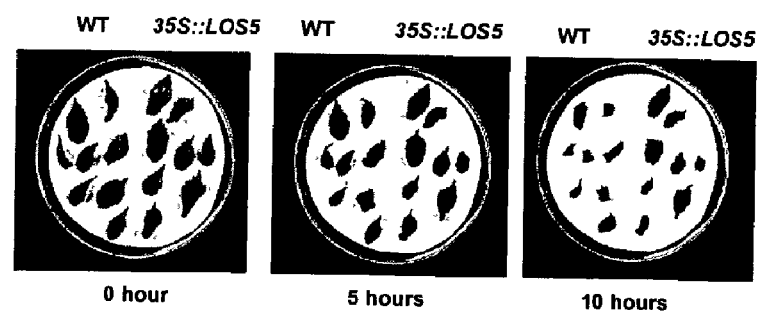

FIG. 12: Reduced water loss rate from leaves of Arabidopsis plants overexpressing the LOS5 gene. Leaves were detached from rosette stage soil-grown seedlings and placed under room conditions under light. Pictures were taken at the indicated time after detachment.

DETAILED DESCRIPTION OF THE INVENTION

Description of the Preferred Embodiments

As described in detail in the Examples below, overexpression the molybdenum cofactor sulfurase described herein provides improved drought resistance in plants. Such plants are also expected to be also more resistant to salt stress and freezing stress. This is because drought tolerance is intimately connected with salt and freezing tolerance, especially with regard to ABA. The loss of function los5 mutants are more sensitive to salt or freezing stress, also suggesting that the overexpression plants are likely more tolerant to salt and freezing stresses. Therefore, in the context of the present invention, the expression "increasing stress tolerance in plants" refers one or any combination the following: increased drought tolerance, increased resistance to salt (i.e., soil salinity), and increased freezing tolerance. As will be readily appreciated by those skilled in the art, the increased tolerance to stress in the plants overexpressing the molybdenum cofactor sulfurase refers to the corresponding plants which do not overexpress this enzyme.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants. Preferred plants include rice, corn, wheat, cotton, peanut, and soybean. Thus, in one embodiment of the present invention, the salt tolerance of a plant can be enhanced or increased by increasing the amount of protein available in the plant, preferably by the enhancement of the molybdenum cofactor sulfurase gene in the plant.

Thus, one embodiment of the present invention are plant cells carrying the polynucleotides of the present invention, and preferably transgenic plants carrying the isolated polynucleotides of the present invention.

As used herein, the term "enhancement" means increasing the intracellular activity of one or more enzymes in a plant cell and/or plant which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, enzyme activity as a whole is increased by preventing the degradation of the enzyme. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

A gene can also be used which encodes a corresponding or variant enzyme with a high activity. Preferably the corresponding enzyme has a greater activity than the native form of the enzyme, more preferably at least in the range of 5, 10, 25% or 50% more activity, most preferably more than twice the activity of the native enzyme.

In the context of the present application, a polynucleotide sequence is "homologous" with he sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to the amino acid sequence which is shown in SEQ ID NO: 2; wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc. Thus, the protein may be from 70% up to less than 100% homologous to SEQ ID NO: 2.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to polynucleotides which contain the complete gene with the polynucleotide sequence corresponding to SEQ ID NO. 1 or fragments thereof, and which can be obtained by screening by means of the hybridization of a corresponding gene bank with a probe which contains the sequence of said polynucleotide corresponding to SEQ ID NO. 1 or a fragment thereof, and isolation of the DNA sequence.

Polynucleotide sequences according to the invention are suitable as hybridization probes for RNA, cDNA and DNA, in order to isolate those cDNAs or genes which exhibit a high degree of similarity to the sequence of SEQ ID NO: 1.

Polynucleotide sequences according to the invention are also suitable as primers for polymerase chain reaction (PCR) for the production of DNA which encodes an enzyme having molybdenum cofactor sulfurase activity.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides according to invention include polypeptides corresponding to SEQ ID NO. 2, and also includes those, at least 70% of which, preferably at least 80% of which, are homologous with the polypeptide corresponding to SEQ ID No. 2, and most preferably those which exhibit a homology of least 90% to 95% with the polypeptide corresponding to SEQ ID NO. 2 and which have molybdenum cofactor sulfurase activity. Thus, the polypeptides may have a homology of from 70% to up to 100% with respect to SEQ ID NO: 2.

The invention also relates to coding DNA sequences which result from SEQ ID NO. 1 by degeneration of the genetic code. In the same manner, the invention further relates to DNA sequences which hybridize with SEQ ID NO. 1 or with parts of SEQ ID NO. 1. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize the function.

In the same manner, the present invention also relates to DNA sequences which hybridize with SEQ ID NO. 1 or with parts of SEQ ID NO. 1. Finally, the present invention relates to DNA sequences which are produced by polymerase chain reaction (PCR) using oligonucleotide primers which result from SEQ ID NO. 1. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C.

Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl, Anal. Biochem., 138:267–284 (1984): Tm=81.5oC.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolated polynucleotides which are substantially similar to the present polynucleotides. In so isolating such a polynucleotide, the polynucleotide can be used as the present polynucleotide in, for example, increasing the salt tolerance of a plant.

One embodiment of the present invention is methods of screening for polynucleotides which have substantial homology to the polynucleotides of the present invention, preferably those polynucleotides encode a protein having molybdenum cofactor sulfurase activity.

The polynucleotide sequences of the present invention can be carried on one or more suitable plasmid vectors, as known in the art for plants or the like.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

In another preferred embodiment the polynucleotide comprises SEQ ID NO: 1, polynucleotides which are complimentary to SEQ ID NO: 1, polynucleotides which are at least 70%, 80% and 90% identical to SEQ ID NO: 1; or those sequence which hybridize under stringent conditions to SEQ ID NO: 1, the stringent conditions comprise washing in 5× SSC at a temperature from 50 to 68° C. Thus, the polynucleotide may be from 70% up to less than 100% identical to SEQ ID NO: 1.

In another preferred embodiment the polynucleotides of the present invention are in a vector and/or a host cell. Preferably, the polynucleotides are in a plant cell or transgenic plant. Preferably, the plant is *Arabidopsis thaliania* or selected from the group consisting of wheat, corn, peanut cotton, oat, and soybean plant. In a preferred embodiment, the polynucleotides are operably linked to a promoter, preferably an inducible promoter.

In another preferred embodiment the present invention provides, a process for screening for polynucleotides which encode a protein having molybdenum cofactor sulfurase activity comprising hybridizing the polynucleotide of the invention to the polynucleotide to be screened; expressing the polynucleotide to produce a protein; and detecting the presence or absence of molybdenum cofactor sulfurase activity in the protein.

In another preferred embodiment, the present invention provides a method for detecting a nucleic acid with at least 70% homology to nucleotide SEQ ID NO: 1, sequences which are complimentary to SEQ ID NO: 1 and/or which encode a protein having the amino acid sequence in SEQ ID NO: 2 comprising contacting a nucleic acid sample with a probe or primer comprising at least 15 consecutive nucleotides of the nucleotide sequence of SEQ ID NO: 1, or at least 15 consecutive nucleotides of the complement thereof.

In another preferred embodiment, the present invention provides a method for producing a nucleic acid with at least 70% homology to the polynucleotides of the present invention comprising contacting a nucleic acid sample with a primer comprising at least 15 consecutive nucleotides of the nucleotide sequence of SEQ ID NO: 1, or at least 15 consecutive nucleotides of the complement thereof.

In another preferred embodiment, the present invention provides a method for making molybdenum cofactor sulfurase protein, comprising culturing the host cell carrying the polynucleotides of the invention for a time and under conditions suitable for expression of molybdenum cofactor sulfurase, and collecting the molybdenum cofactor sulfurase protein.

In another preferred embodiment, the present invention provides a method of making a transgenic plant comprising introducing the polynucleotides of the invention into the plant.

In another preferred embodiment, the present invention provides method of increasing the salt tolerance of a plant in need thereof, comprising introducing the polynucleotides of the invention into said plant.

Methods, vectors, and compositions for transforming plants and plant cells in accordance with the invention are well-known to those skilled in the art, and are not particularly limited. For a descriptive example see Karimi et al., TRENDS in Plant Science, Vol. 7, No. 5, May 2002, pp. 193–195, incorporated herein by reference.

In another preferred embodiment, the present invention provides an isolated polypeptide comprising the amino acid sequence in SEQ ID NO: 2 or those proteins that are at least 70%, preferably 80%, preferably 90% and preferably 95% identity to SEQ ID NO: 2, where the polypeptides have molybdenum cofactor sulfurase activity. Thus, the enzyme has a homology of from 70% to less than 100% homology to SEQ ID NO: 2.

To understand low temperature and osmotic stress signaling in plants, we isolated and characterized two allelic Arabidopsis mutants, los5-1 and los5-2, which are impaired in gene induction by cold and osmotic stresses. Expression of RD29A-LUC (firefly luciferase reporter gene under control of the stress responsive RD29A promoter) in response to cold and salt/drought is reduced in the los5 mutants but the response to ABA remains unaltered. RNA blot analysis indicates that the los5 mutation reduces the induction of several stress-responsive genes by cold and severely diminishes or even completely blocks the induction of RD29A, COR15, COR47, RD22, and P5CS by osmotic stresses. los5 mutant plants are compromised in their tolerance to freezing, salt or drought stress. los5 plants are ABA-deficient, as indicated by increased transpirational water loss and reduced accumulation of ABA under drought stress in the mutant. A comparison with another ABA deficient mutant aba1 reveals that the impaired low temperature gene regulation is specific to the los5 mutation. Genetic tests suggest that los5 is allelic to aba3. Map-based cloning reveals that LOS5/ABA3 encodes a molybdenum cofactor (MoCo) sulfurase. MoCo sulfurase catalyzes the generation of sulfurylated form of MoCo, a cofactor required by aldehyde oxidase that functions in the last step of ABA biosynthesis in plants. The LOS5/ABA3 gene is expressed ubiquitously in different plant parts and the expression level increases in response to drought, salt, or ABA treatment. Our results show that LOS5/ABA3 is a key regulator of ABA biosynthesis, stress-responsive gene expression and stress tolerance.

Results

Isolation of Arabidopsis Mutants with Reduced RD29A-LUC Induction by Salt Stress Seeds from Arabidopsis plants expressing the RD29A-LUC transgene (referred to as wild type) were mutagenized with ethyl methanesulfonate (EMS) and seedlings of the $M_2$ generation were screened for mutants with altered regulation of the transgene (Ishitani et al., 1997). One group of mutants was isolated that exhibit a clear reduction in NaCl-induced luminescence. Two allelic mutants, designated as los5 (los1 to los4 are mutants with specific defects in low temperature signaling, J.-K. Zhu, unpublished data), that show reduced luminescence induction in response to both NaCl and cold, were chosen for detailed characterization.

Figure 1:
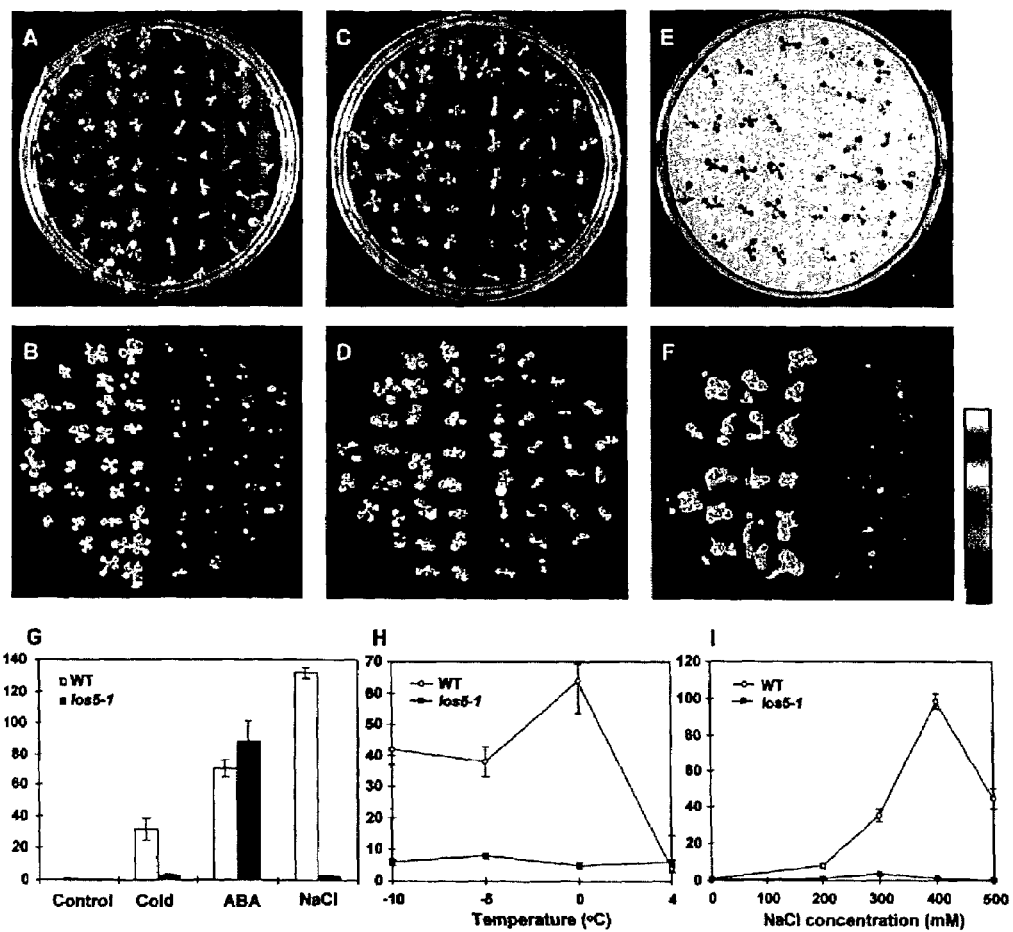
FIG. 1: Luminescence phenotypes of los5 mutant plants.
(A) Morphology of wild-type (left) and los5-1 (right) seedlings on an agar plate.
(B) Luminescence of (A) after low-temperature treatment at 0° C. for 48 hr.
(C) Morphology of wild-type (left) and los5-1 (right) seedlings on an agar plate.
(D) Luminescence after treatment with 100 μM ABA for 4 hr.
(E) Morphology of wild-type (left) and los5-1 (right) seedlings on filter paper saturated with 300 mM NaCl.
(F) Luminescence of (E) after 5 hr of 300 mM NaCl treatment.
(G) Quantitation of the luminescence intensities of wild type and los5-1 plants in response to cold (0° C. for 48 hr), ABA (100 μM for 4 hr), or NaCl (300 mM for 5 hr) treatment as shown in FIGS. 1B, 1D, and 1F. Also shown are those of untreated plants (control).
(H) Low temperature dosage-response curve. Treatments at −5° C. or −10° C. lasted for 3 hr following by incubating at room temperature for 2 hr. Treatment at other temperatures lasted for 48 hr before imaging.
(I) NaCl dosage-response curve. Treatment time was 3 hr.

As shown in FIG. 1, the luminescence intensities in los5-1 mutant seedlings were considerably lower than those in the wild type when treated with cold (0° C.) for 48 hr (FIG. 1B) or 300 mM NaCl for 5 hr (FIG. 1F). In contrast, the luminescence expression in response to ABA (100 μM for 5 hr) is not lower than that in the wild type (FIG. 1D). Without stress treatment there was virtually no luminescence expression in either the wild type or los5 mutant. Quantification of the luminescence intensities in FIG. 1 indicates that the levels of RD29A-LUC expression in los5-1 seedlings are only 8% and 2% of the wild-type levels for cold and NaCl treatments, respectively, whereas the expression levels under ABA treatment are virtually the same for the mutant and wild type (FIG. 1G).

To determine whether the los5 mutant has an altered threshold response to either cold or salt stress, different low temperatures or NaCl dosages were applied and the luminescence expression in los5 and wild type plants was quantified. Results show that los5 mutant plants exhibited a consistently lower luminescence expression under the temperatures tested (FIG. 1H), and increased NaCl concentrations also did not result in a recovery of the expression to the wild type levels (FIG. 1I). This indicates that the reduced responsiveness to cold or osmotic stress in los5 is not due to altered induction thresholds of these stresses.

los5-1 mutant plants were backcrossed to the wild type plants. Analysis of luminescence expression of the $F_1$ seedlings and the selfed $F_2$ population indicated that los5 is a recessive mutation in a nuclear gene (Table 1). Pairwise crosses with other mutants that also show reduced luminescence responses to NaCl treatment identified a second allele, los5-2 (Table 1). The los5-2 mutant has identical phenotypes as los5-1 (data not shown).

Reduced Gene Regulation by Salt, Drought, and Cold in los5 Mutants

To assess whether the los5 mutation has a similar effect on expression of the endogenous RD29A as it has on the RD29A-LUC transgene, RNA blot analysis was carried out with total RNA isolated from los5-1 and wild type seedlings that were not stress-treated (control), or treated with either cold (0° C.) for 24 hr, 100 μM ABA for 2 hr, 300 mM NaCl for 3 hr, or 30% PEG for 5 hr. The results show that whereas ABA induction of the endogenous RD29A was not substantially affected, NaCl induction was almost completely blocked by the los5 mutation (FIG. 2). The mutation also clearly reduced RD29A expression in response to cold treatment. To distinguish whether the effect of NaCl is due to ionic or osmotic stress, polyethylene glycol (PEG, average molecular weight 6,000) was used. The steady-state transcript level of RD29A was also greatly reduced in los5 in response to PEG treatment (FIG. 2). This indicates that the los5 mutation reduces gene expression under osmotic stress.

The los5 mutation also has dramatic effects on the expression of other stress-responsive genes under osmotic or cold stress treatment. Several stress-responsive genes including COR15A (Lin and Thomashow, 1992), KIN1 (Kurkela and Franck, 1990), COR47 (Gilmour et al., 1992), RD22 (Yamaguchi-Shinozaki et al., 1992), P5CS were analyzed. The los5 mutation almost completely blocks the osmotic stress induction of COR15A, KIN1, and P5CS (FIG. 2). It also substantially reduces the induction of RD22 and COR47 by NaCl and PEG. Interestingly, whereas ABA-induction of COR47 is enhanced by the los5 mutation, the induction of COR15A and P5CS by ABA is reduced by the mutation (FIG. 2). As a control, the transcript level of an actin gene was determined and the result shows that its expression is not changed by stress treatments and not substantially different between the mutant and the wild type under the respective treatments (FIG. 2).

los5 Mutant Plants are More Sensitive to Freezing Stress

The reduced expression of RD29A and other stress-responsive genes in los5 might have an impact on the stress tolerance of the mutant plants. To test the sensitivity of los5 mutant plants to low temperature, los5-1 and wild type plants were incubated at 4° C. for up to 4 weeks. No significant difference in growth was found between the mutant and wild type, indicating that LOS5 is not critical for chilling resistance. To test whether los5 mutant plants are defective in cold acclimation, wild type and los5-1 rosette plants growing in soil (FIG. 3A) was cold-acclimated (4° C. under light) for 48 hr. The plants were then treated at −7° C. for 5 hr. After incubation in the growth chamber for one day, clear difference was observed: whereas 97% of the wild type plants survived −7° C. freezing, all los5-1 mutant plants were killed (FIG. 3B and data not shown). The result shows that los5 mutant plants have reduced freezing tolerance.

los5 Mutant Plants are More Sensitive to Drought and Salt Stress Damage

Steady-state RNA levels as shown in FIG. 2 have revealed a remarkable reduction in los5-1 mutant plants in the expression of stress-responsive genes in response to salt or drought (i.e., PEG) treatments. Except for the P5CS ($\Delta^1$-pyrroline-5-carboxylate synthase) gene, the function of most the genes examined is not clear. P5CS catalyzes the rate-limiting step in the biosynthesis of proline, a major osmolyte important for plant tolerance to freezing, drought, and salt stresses (e.g., Xin and Browse, 1998; Roosens et al., 1999; Hong et al., 2000). Proline contents in wild type and los5-1 plants treated with ABA or salt stress were measured. In the absence of stress treatment (i.e. control), los5-1 mutant plants had a slightly higher proline content than wild type plants. The proline content in both los5-1 and the wild-type plants increased in response to 150 mM NaCl treatment. However, the increase in los5-1 plants is less than that in wild-type plants. los5-1 mutant and the wild-type plants had similar proline contents when treated with 50 μM ABA (FIG. 4A).

To determine the drought sensitivity in los5 mutant plants, los5-1 and wild type seedlings were treated with 30% PEG and electrolyte leakage was measured as an indicator of drought-induced cellular damage. While los5-1 seedlings had higher electrolyte leakage than the wild type even without stress treatment, PEG treatment resulted in an electrolyte leakage in the mutant that is twice as much as in wild type plants (FIG. 4B), indicating that los5 mutant plants are more sensitive to drought stress.

Although los5-1 mutant seeds were more tolerant to NaCl stress at germination, mutant root growth did not differ from that of the wild type in their NaCl sensitivity (data not shown). Despite similar levels of inhibition of root growth by NaCl stress, los5-1 mutant plants did show increased sensitivity to NaCl in the shoot. At NaCl concentrations of 75 mM or higher, los5-1 mutant seedlings became yellowish and were killed by prolonged exposure to the stress, whereas wild type plants survived (FIG. 4C, and data not shown).

LOS5 Mutant Plants are Deficient in Stress-induced ABA Accumulation

In addition to changes in stress sensitivity, los5 mutant plants are also altered in development. Under our long day growth conditions, los5-1 plants flowered approximately 5 days earlier than wild type plants. Besides having a more dark green color, los5-1 mutant leaves are narrower and slightly serrated in the edge, as compared to the more round leaves of wild type plants (FIGS. 5A and 5B). In fact, los5 mutant plants can be distinguished from the wild type based on these leaf characteristics. These visible phenotypes are shared by the los5-2 mutant plants, co-segregate with the los5 luminescence phenotypes, and are present in los5-1 plants that had been backcrossed with the wild type for 4 times.

When the aboveground parts are detached from the roots at the rosette stage (FIG. 5C), the younger leaves of los5-1 plants withered within 10 min under our room conditions (22±2° C., ~30% relative humidity). In contrast, wild type leaves remained turgid under the same conditions (FIG. 5D). The inflorescence of adult los5 plants also readily became wilty when the plants were removed from growth chambers (22° C.±2° C., 90% relative humidity) to our room conditions, whereas the wild type inflorescence remained turgid (FIG. 5E). These observations suggest that los5 mutant plants may have a higher transpiration rate. Measurement of transpirational water loss shows that los5 mutant plants indeed lost water much faster than wild type plants (FIG. 5F), indicating potential defects in stomatal regulation, which is a typical phenotype of ABA deficient or insensitive mutants.

To determine whether los5 mutant plants are deficient in ABA or are insensitive to ABA, wild type and los5-1 plants at the rosette stage were sprayed with 100 μM ABA 3 hr before detaching the aerial parts for water loss measurement. FIG. 5F shows whereas the ABA treatment did not significantly affect transpirational water loss from wild type plants, the treatment reduced substantially the rate of water loss from los5-1 plants. This observation is consistent with ABA deficiency in los5-1 mutant plants and suggests that los5-1 is not ABA-insensitive.

ABA contents in los5-1 and wild type plants were measured by using an immunoassay. In the absence of stress treatment, ABA contents in the wild type and los5-1 leaves are essentially the same (Table 2). When detached leaves were allowed to lose 30% of their fresh weight, ABA contents in both the wild type and los5-1 mutant increased. However, the magnitudes of the increases are quite different. Whereas ABA content in the wild type increased by more than 300% in response to the water stress, the increase in los5 leaves was only 80%, with the wild type having nearly 250% as much ABA as in the mutant (Table 2).

These data clearly show that los5-1 is an ABA deficient mutant. To test whether los5 is allelic to known ABA deficient mutants, los5-1 was initially crossed with aba1 and aba2. Analysis of the $F_1$ plants indicated that los5-1 is not allelic to either one (Table 1 and data not shown). When the aba3-1 mutant became available later, we crossed it to los5-1 and analyzed the phenotypes of $F_1$ and $F_2$ seedlings by luciferase imaging and water loss measurement. Luminescence images showed that the resulting $F_1$ seedlings had a low expression of luminescence when treated with 300 mM NaCl, indicating los5 is likely allelic to aba3. However, measurement of transpirational water loss in the $F_1$ seedlings was less conclusive in part because when crossed to the wild type RD29A-LUC plants (C24 background), the aba3/ABA3 heterozygous plants showed an incomplete recessive phenotype, i.e., the $F_1$ plants lost water slower than aba3 but faster than the RD29A-LUC wild type. Although the $F_1$ plants (los5/aba3) from a cross between los5-1 and aba3-1 lost water faster than the $F_1$ plants from a cross between RD29A-LUC wild type and aba3-1, the water loss rate of los5-1/aba3-1 heterozygous plants was still lower than either los5-1 or aba3-1 mutant (data not shown). The intermediate phenotypes probably have to do with the genetic differences between the two ecotypes (C24 vs. Columbia).

LOS5 Regulates Cold- and Osmotic Stress-responsive Gene Expression Through Distinct Mechanisms Gene expression analysis in los5-1 mutant plants suggests a critical role of LOS5 in the regulation of stress-responsive genes by salt and drought and to a less extent, by cold (FIG. 1 and FIG. 2). In our mutant screen, a second genetic locus, LOS6, was defined by los6-1 mutant plants that show reduced gene induction by salt/drought treatments (J.-K. Zhu, unpublished observation). Interestingly, genetic analysis showed that los6 is allelic to aba1. This provides an excellent opportunity to study the role of ABA in cold and osmotic stress regulation of gene expression by using the very sensitive and reliable RD29A-LUC reporter and comparing two different ABA deficient mutants, los5 and los6. RD29A-LUC induction by salt stress is significantly reduced in los5 and los6 (FIG. 6A). Interestingly, when ABA was simultaneously administered with salt stress, RD29A-LUC expression in both los5 and los6/aba1 were restored to the wild type level or higher, indicating that exogenous ABA complements the reduced salt induction phenotype. This suggests that reduced gene induction by salt and drought in both los5-1 and los6/aba1 mutants can be solely accounted for by ABA deficiency.

Gene induction by cold was also analyzed using these two mutants. Without stress treatment, los6, like los5 and the wild type, did not show any luminescence expression (data not shown). To our surprise, whereas cold induction of RD29A-LUC in los5-1 is significantly reduced, the expression in los6/aba1 is significantly increased (FIG. 6B). This increased luminescence expression in los6 was consistently observed in numerous independent experiments. To test the role of ABA in cold gene regulation, ABA was administered together with cold treatment. Measurement of RD29A-LUC expression shows that ABA treatment restored the luminescence expression in los6/aba1 close to the wild type level (FIG. 6B), indicating that the elevated cold induction in los6/aba1 may be an indirect consequence of ABA deficiency. In contrast, application of ABA to los5 mutant seedlings failed to restore RD29A-LUC expression to the wild type level. In fact, los5 plants did not appear to respond to this ABA treatment as compared to cold treatment alone (FIG. 6B), suggesting that the reduced gene induction by cold in los5 mutants is not a result of ABA deficiency.

Map-based Cloning of the LOS5 Gene

To clone the LOS5 gene, homozygous los5-1 mutant plants in the C24 ecotype were crossed with wild type plants in the Columbia ecotype. The resulting $F_1$ plants were allowed to self. Initially, the $F_2$ seeds were plated on MS agar plates and seedlings were analyzed for luminescence expression. Putative mutants were selected by their reduced luminescence expression under cold treatment as well as salt treatment. Selected seedlings were then transferred to soil and adult plants were tested for the wilty phenotype under reduced humidity conditions. Simple sequence length polymorphism (SSLP) markers distributed throughout the five Arabidopsis chromosomes that exhibit a size polymorphism between C24 and Columbia ecotypes were used for genetic mapping. The genetic mapping placed the LOS5 locus to the upper arm of chromosome I, between the SSLP markers AtEAT1 and nga248 (FIG. 7A). This region corresponds roughly to where the ABA3 locus was mapped (Léon-Kloosterzie et al., 1996). As most of the mutant seedlings selected after the NaCl treatment failed to survive, we later used the salt tolerance phenotype of los5 mutant seeds during germination to select mutants for mapping. Specifically, the segregating $F_2$ seeds were plated on agar medium supplemented with 200 mM NaCl, a salt concentration that inhibits the germination of wild type but not los5 mutant seeds. Putative los5 seedlings were then transferred to soil and later confirmed by examination of their wilty phenotype.

While the fine mapping of LOS5 was in progress, genomic DNA sequence corresponding to the LOS5 region was released. Given the ABA deficiency phenotype, the availability of genomic sequence makes it possible to select candidate genes to find the los5 mutation. A detailed examination of the genes on BAC clones in this region identified several candidates that could potentially function in ABA biosynthesis. Among them, the F19K19.13 gene on the BAC clone F19K19 appears to be a good candidate (FIG. 7A). BLAST searches suggest that the predicated gene product has high similarity to molybdenum cofactor sulfurase from other organisms. Previous studies have indicated that the genetic lesion in aba3 is in the introduction of S into the molybdenum cofactor (MoCo) (Schwartz et al., 1997a) and sulfurylated MoCo is required by aldehyde oxidase (Schwartz et al., 1997a; Akaba et al., 1998; Sagi et al., 1999) which functions in the last step of ABA biosynthesis (Schwartz et al., 1997a).

Genomic DNA corresponding to F19K19.13 was amplified by PCR from wild type and los5-1 mutant plants and sequenced. Comparison between the sequences revealed a G to A change 1083 bp downstream of the predicted translation initiation codon in los5-1. The F19K19.13 gene was then amplified from los5-2 and sequenced. Sequence analysis identified a G to A change in los5-2, 1040 bp downstream of the predicted translation initiation codon. These results strongly suggest that the F19K19.13 gene is LOS5.

The F19K19.13 gene product is predicted to function in ABA biosynthesis at a step corresponding to ABA3. Our genetic analysis also suggested that los5-1 is likely allelic to aba3-1 (Table 2). Taken together, these results strongly suggested that F19K19.13 is the ABA3/LOS5 gene. To test this hypothesis, we sequenced the F19K19.13 gene from aba3-1 and aba3-2 alleles, and the DNA sequences were compared with those from Columbia (aba3-1 background) and Landsberg (aba3-2 background) wild type plants, respectively. Results showed that in aba3-1, a G to A change occurred at position 3707 while in the aba3-2 allele, there are three mutations in a row with a single non-mutated nucleotide spacing them: a G to A change at position 3176, a T to A change at position 3178, and a deletion of T at position 3180. The nature of the mutations is consistent with the type of mutagens used: aba3-1 was caused by EMS, while aba3-2 was caused by γ-ray irradiation (Léon-Kloosterzie et al., 1996).

All the changes in F19K19.13 DNA sequence in the four los5/aba3 mutant alleles are predicted to cause changes in the predicted open reading frame. Together, the above data unequivocally demonstrate that the LOS5 locus is identical to ABA3, and the LOS5/ABA3 gene is F19K19.13. After we have identified the los5 mutation, a third mutant allele of ABA3, frs1/aba3-3, was recently reported (Llorente et al., 2000). The freezing sensitive phenotype and the degree of ABA deficiency in frs1/aba3-3 (Llorente et al., 2000) are very similar to those in los5. For consistency, we propose to rename los5-1 as aba3-4, and los5-2 as aba3-5.

LOS5/ABA3 Encodes a Molybdopterin Cofactor Sulfurase

To obtain the cDNA sequence of LOS5, reverse transcriptase-PCR was carried out with mRNA extracted from wild type Columbia plants. The RT-PCR product was cloned and sequenced (accession number AY034895). After the LOS5 cDNA was cloned, an identical sequence (accession number AF325457, submitted by Bittner F. and Mendel R. R.) was released in the Genebank. Comparison with genomic DNA sequence revealed that the LOS5 gene consists of 21 exons and 20 introns (FIG. 7B). The open reading frame consists of 2457 nucleotides and is predicted to encode a protein of 819 amino acids with an estimated molecular weight of 91.8 kDa. The nucleic acid and amino acid sequences are shown in FIG. 8 (SEQ ID NO: 1 and 2).

The los5-1 mutation occurred at the $4^{th}$ exon and changes a tryptophan residue at amino acid position 120 to a stop codon and thereby truncates the protein. The los5-2 mutation also occurred at the 4th exon and changes a small glycine residue at position 106 to a larger, negatively charged glutamic acid residue. The aba3-1 mutation occurred at the $13^{th}$ exon and changes a glycine at position 469 to a glutamic acid residue. The aba3-2 mutations occurred at the junction between 10$^{th}$ and 11$^{th}$ exons. The aba3-2 mutation changes the leucine residue at position 387 to a stop codon and thereby truncates the protein from the 11$^{th}$ exon (FIGS. 7B and 8).

Database searches showed that LOS5/ABA3 has high sequence homology to the molybdopterin cofactor sulfurase (MCSU) recently identified from cattle (Watanabe et al., 2000), which belongs to a highly conserved protein family found from bacteria to human (FIG. 9). Overall, the LOS5 protein has 35% amino acid sequence identity and 53% similarity to the human homolog, 34% identity and 49% similarity to the Mal protein of Drosophila melanogaster, 35% identity and 51% similarity to MCSU of cattle (Watanabe et al., 2000), and 31% identity and 48% similarity to the HxB protein of Aspergillus nidulans (Amrani et al., 1999). The entire sequence of LOS5/ABA3 appears to consist of three domains. The N-terminal domain shows high sequence homology to the Class V pyridoxal 5'-phosphate-dependent aminotransferases of type I fold, represented by the isopenicillin N epimerase, phosphoserine aminotransferase, aspartate decarboxylase, the small subunit of cyanobacterial soluble hydrogenase and the NifS proteins from Azotobacter vinelandii. Recently, the structures of several NifS-like proteins were solved (Fujii et al., 2000; Kaiser et al., 2000), thus making it possible to identify conserved motifs in the NifS-like domain of LOS5/ABA3 (FIG. 7C). This includes a putative pyridoxal phosphate binding motif and a conserved cysteine motif (FIG. 7C). The respective key residues in these motifs are marked in FIG. 10. It is noteworthy that several putative proteins in the Arabidopsis genome show significant sequence similarity to this NifS-like domain (data not shown). The second domain, the junction that connects the NifS-like domain to the C-terminal domain shows little sequence homology to other proteins except among members of this MCSU family. The C-terminal domain shows significant sequence similarity with a group of unknown proteins found both in Arabidopsis and in other organisms. However, the Arabidopsis genome does not contain any other protein with significant overall sequence homology to the full-length LOS5/ABA3 protein, implying that LOS5/ABA3 is a single copy gene in the genome.

LOS5/ABA3 is Ubiquitously Expressed and its Expression is Enhanced by ABA and Drought Stress To analyze the expression pattern of the LOS5/ABA3 gene, full-length LOS5 cDNA was used as a probe in RNA blot analysis, using total RNA extracted from different parts of unstressed wild type plants. The result indicates that LO5 is constitutively expressed at a relatively low level in all plant parts examined, including roots, stems, leaves, flowers and siliques (FIG. 10A). Interestingly, the transcript level of LOS5 increases significantly in response to drought (FIG. 10B), ABA, NaCl or PEG treatments (FIG. 10C). Cold treatment has no significant effect on LOS5 expression (FIGS. 10C and 10D). The steady-state LOS5 transcript levels in los5-1 seedlings are considerably lower than those in the wild type under the treatment conditions (FIG. 10D), suggesting that the mutant transcript with a pre-mature stop codon may trigger RNA surveillance mechanisms that remove abnormal transcripts (Hilleren and Parker, 1999).

The expression of LOS5 was also analyzed in another ABA deficient mutant, aba1-1 (Koornneef et al., 1982), and in an ABA-insensitive mutant, abi1-1 (Koornneef et al., 1984). The results indicate that the induction of LOS5 by osmotic stress in aba1 is not substantially different from that in the wild type. In the abi1-1 mutant, the induction of LOS5 appears slightly lower compared to that in the wild type (FIG. 10D).

Comparison between the Effects of los5/aba3, aba1 and abi1 Mutations on Stress Gene Regulation In contrast to los5-1, the aba1-1 mutation does not decrease the induction of the RD29A transcript by cold or ABA (FIG. 10D). In fact, cold induction of RD29A appears higher in aba1-1 compared to that in the wild type. The aba1-1 mutation does decrease the induction of RD29A by NaCl or PEG stress, although the effect is not as dramatic as that of los5-1. The different effects on RD29A transcript induction by los5-1 and aba1-1 are in general agreement with the findings on the effects of los5-1 and los6-1 (a different aba1 allele) on RD29A-LUC expression (FIG. 6). aba1-1 enhances ADH induction by cold and ABA but decreases the induction by NaCl or PEG stress (FIG. 10D). This is again in sharp contrast with the los5-1 mutation, which decreases the ADH induction by either cold, ABA, NaCl or PEG (FIG. 10D). Both aba1-1 and los5-1 nearly completely blocks RAB18 induction by osmotic stresses (FIG. 10D). However, los5-1 but not aba1-1, also blocks RAB18 induction by ABA (FIG. 10D). Compared with aba1-1 or los5-1, the abi1-1 mutation has little effect on RD29A or ADH induction by the stresses (FIG. 10D). Nevertheless, the induction of RAB18 by ABA, NaCl or PEG is reduced in the abi1-1 mutant (FIG. 10D).

Because CBF (Stockinger et al., 1997) and DREB2 (Liu et al., 1998) family of transcription factors are known to bind to the DRE element present in the promoters of RD29A and several other stress responsive genes, we were interested in determining whether stress induction of these transcription factors is affected by the ABA deficient or insensitive mutations. The results show that the expression of the cold-specific CBF2/DREB1C is not significantly affected by los5-1/aba3-4 or aba3-1, but is enhanced in the aba2-1 mutant (FIG. 10E). It was reported that DREB2A is induced specifically by osmotic stress (Liu et al., 1998). Under our treatment conditions, DREB2A expression is also up-regulated by cold stress. Interestingly, whereas none of the ABA-deficient mutations significantly affects osmotic stress-induction of DREB2A, los5 shows increased cold-induction of DREB2A compared to the wild type (FIG. 10E).

Discussion

The phytohormone ABA plays many significant roles in plant growth and development, and in plant responses to environmental stresses. Understanding ABA biosynthesis pathways in plants is thus of critical importance. ABA biosynthesis mutants serve as excellent tools to for understanding ABA biosynthesis and for studying gene regulation in response to stressful environments. In Arabidopsis and other plants such as maize, tobacco, and tomato, genetic analysis based on ABA promotion of seed dormancy has yielded a series of mutants that are defective in ABA biosynthesis (for recent review, see Koornneef et al., 1998; Cutler and Krochko, 1999; Loitenberg et al., 1999). Characterization of these mutants along with biochemical studies has revealed that in plants ABA is synthesized from an 'indirect' pathway via the cleavage of a carotenoid precursor. The Arabidopsis aba1 mutant (and tobacco aba2) is defective in the epoxidation of zeaxanthin and antheraxanthin to violaxanthin (Rock and Zeevaart, 1991) and the affected gene encodes a zeaxanthin epoxidase (Marin et al., 1996). Oxidative cleavage of the 9-cis-neoxanthin by the VP14 protein yields xanthoxin. The VP14 gene was isolated by using the maize vp14 mutant (Tan et al., 1997) and encodes a 9-cis-epoxycarotenoid dioxygenase (NCED) (Schwartz et al., 1997b). It is thought that xanthoxin is converted to ABA by a two-step reaction via AB-aldehyde. The Arabidopsis aba2 mutant is impaired in the first step of this reaction, thus unable to convert xanthoxin into AB-aldehyde. The Arabidopsis aba3 mutant is defective in the last step of ABA biosynthesis, i.e. the conversion of AB-aldehyde to ABA (Schwartz et al., 1997a), which is catalyzed by AB-aldehyde oxidase. Mutations in either the aldehyde oxidase apoprotein (e.g., Seo et al., 2000b) or molybdenum cofactor (MoCo) synthase impair ABA biosynthesis and lead to ABA deficiency in plants.

Molybdenum cofactor consists of a single Mo atom coordinated to the sulfur atoms of an organic moiety, molybdopterin. MoCo is highly conserved in cellular organisms and is used for the transfer of an oxygen atom in redox reactions involved in the metabolism of nitrogen, sulfur, and carbon (for review, see Kisher et al., 1997). Defects in MoCo biosynthesis have been reported to be associated with many diseases in humans and other animals (for review, see Reiss, 2000). In plants, three groups of MoCo-containing enzymes have been described (for review, see Mendel and Schwarz, 1999): nitrate reductase (NR), xanthine dehydrogenase (XDH) and aldehyde oxidase (AO). A fourth group, sulfite oxidase, also exists in the completely sequenced Arabidopsis genome. Different from nitrate reductase and sulfite oxidase that use dioxyo form of MoCo, however, both xanthine dehydrogenase and aldehyde oxidase require that the MoCo be modified in the last step of biosynthesis with the insertion of a sulfur atom to replace one of the two terminal oxygen atoms (FIG. 11). This sulfuration reaction is catalyzed by molybdopterin cofactor sulfurase (MCSU). Mutants defective in this step have been identified from *Drosophila melanogaster* (maroon-like, mal) (Wahl et al., 1982), *Aspergillus nidulans* (hxB) (Scazzocchio, 1973; Amrani et al., 1999) and cattle (Watanabe et al., 2000). Plant mutants defective in this sulfuration step have also been identified, i.e., tobacco aba1 (Leydecker et al., 1995), tomato flacca (Marin and Marion-Poll, 1997), and Arabidopsis aba3 (Schwartz et al., 1997a). Biochemical characterizations suggest that these plant mutants are all defective in the last step of ABA biosynthesis. As expected, the defects are specific to AO and XDH but not to NR (Leydecker et al., 1995; Marin and Marion-Poll, 1997; Schwartz et al., 1997a). Like in the *Drosophila mal* mutant, resulfuration of the plant mutant extracts with $Na_2S$ restores XDH and AO activities in Arabidopsis aba3 (Schwartz et al., 1997a), tobacco aba1 (Akaba et al., 1998), and tomato flacca (Sagi et al., 1999). These previous studies suggest that the wild type genes corresponding to the respective mutations likely encode molybdenum cofactor sulfurases that function in the last step of MoCo modification, which is specifically required by aldehyde oxidases and xanthine dehydrogenases for their catalytic activities.

The identification of los5 mutants as impaired in ABA biosynthesis and the cloning of the LOS5/ABA3 gene demonstrate that indeed LOS5/ABA3 encodes a putative molybdenum cofactor sulfurase (MCSU). As free molybdenum cofactor is extremely unstable, to date there has been no report on sulfuration enzyme activity of MCSU using either MoCo or other substrates. Nonetheless, abundant evidence both from plant and animal studies that resulfuration of mutant extracts restores AO and XDH or other enzyme activities strongly suggests that MCSU have in vivo sulfuration activity against the desulfo form of MoCo. Additionally, sequence comparisons with other proteins also support the potential catalytic property of MCSU.

Like other MCSU proteins, the LOS5/ABA3 gene product has extensive sequence similarity to the NifS-like protein in its N-terminal region (FIG. 7C). The NifS protein of *Azotobacter vinelandii* is required for the activity of nitrogenase, the only Mo-containing enzyme that does not use molybdopterin cofactor but instead requires an iron-molybdenum-sulfur cluster for electron transfer. Although the exact function of NifS protein in nitrogen fixation is not known, NifS in vitro was shown to be able to use L-cysteine as a substrate to form alanine and sulfide. Thus, NifS appears to act as a cysteine desulfurase in the biogenesis of the metallocluster by mobilizing an inorganic sulfide originated from the substrate L-cysteine (Zheng et al., 1993). This reaction is quite similar to the chemical reactions expected to be catalyzed by LOS5/ABA3 in the sulfuration of the desulfo-MoCo. In fact, both the pyridoxal phosphate binding motif and the conserved cysteine motif required for NifS are all well conserved in LOS5/ABA3 and its homologs in other organisms (FIGS. 7C and 8). Both by analogy with members of the class V aminotransferase-like proteins and by experimental analysis (Zheng et al., 1993), pyridoxal phosphate (PLP) was found to be a cofactor for NifS protein. Given the high similarity with NifS and other PLP-dependent proteins in this class, it is likely that PLP is also a cofactor for LOS5/ABA3. By comparing LOS5/ABA3 with other NifS proteins whose structures were recently solved (Fujii et al., 2000; Kaiser et al., 2000), the conserved lysine at position 271 (FIG. 9) is probably the residue where PLP is covalently attached to make an Schiff base (Fujii et al., 2000). Likewise, the conserved cysteine residue at position 430 (FIG. 10) is a likely S donor for the trans-sulfuration reaction (FIG. 11). Both conserved motifs are found in all LOS5/ABA3 homologs (FIG. 10). It is expected that both the PLP and the Cysteine motifs are required for the catalytic activity of LOS5/ABA3. Interestingly, the aba3-1 mutation occurs just outside of the NifS-like domain, but is still in a highly conserved region, suggesting that this region is also required for the enzyme function.

The overall structure of LOS5/ABA3 is reminiscent of a chimeric protein that has evolved by fusing two separate proteins. The C-terminal domain does not have a known function yet, but is likely also important, considering the high similarity in this domain among the MCSU proteins from diverse organisms, and its high similarity to several unknown proteins in the Arabidopsis genome.

One interesting note related to the apparently multiple functional domain structure is that both the los5-1 and los5-2 mutants have a unique leaf morphology (FIG. 5B), whereas in aba3-1 and aba3-2, there is no such clear alteration in leaf form (data not shown). It is worth noting that both the los5-1 and los5-2 mutations occurred at the N-terminal part, whereas the aba3-1 and aba3-2 mutations occurred at the middle of the protein. It is therefore tempting to speculate that the N-terminal domain in the aba3-1 and aba3-2 mutant proteins may still have some activity that is required for maintenance of the wild type leaf morphology. On the other hand, the los5-1 and los5-2 mutant forms may have lost this activity, resulting in an altered leaf form.

Since LOS5/ABA3 is a single copy gene in the Arabidopsis genome, it is not surprising that it is ubiquitously expressed (FIG. 10A). This is in contrast with the aldehyde oxidase (AAO) gene family where each member has a different expression pattern (Seo et al., 2000b). However, it is interesting to note that the tomato flacca mutant was reported to lose AO and XDH activities in the shoot but retain measurable activities in the roots where a notable amount of ABA accumulates (Sagi et al., 1999). This raises the possibility that there may exist more than one LOS5/ABA3-like MCSU genes in tomato, and a root-specific isoform(s) may remain active in the flacca mutant. In addition to impaired ABA biosynthesis in flacca mutant shoot, it was shown that the mutation might reduce the transport of ABA from the root to shoot as well (Sagi et al., 1999).

In the present study, we showed that the expression of the LOS5/ABA3 gene is up-regulated when plants are treated with drought, salt or ABA (FIG. 10). We note that the promoter region of LOS5/ABA3 contains putative ABREs (e.g. ACGTGG at −253 upstream from translation initiation codon) and DRE/CRT-like elements, suggesting that the LOS5/ABA3 gene may be regulated by ABA and drought/salt stress in a way similar to other stress-responsive genes. In the ABA biosynthesis pathway, it is generally thought that the rate-limiting step is in the oxidative cleavage of the 9-cis-neoxanthin catalyzed by the VP14 protein (Tan et al., 1997; Schwartz et al., 1997b; Loitenberg et al., 1999; Iuchi et al., 2000; Thompson et al., 2000; Taylor et al., 2000). Given the relative low abundance of LOS5/ABA3 transcript and the fact it is the only gene encoding MCSU in Arabidopsis, it is likely that LOS5/ABA3 may also regulate ABA biosynthesis. Low temperature appears to have little effect on the expression of LOS5/ABA3 (FIGS. 9C and 9D), consistent with its limited effect on endogenous ABA biosynthesis (Thomashow, 1999). Qin and Zeevaart (1999) also found that low temperature did not induce the expression of PvNECD1 (a VP14 homolog in bean). Drought treatments (20% fresh weight loss and incubated for 3 or 6 hr) significantly increased the expression of LOS5/ABA3 (FIG. 10B), yet the same treatments failed to up-regulate AAO3 gene expression (data not shown). This lack of AAO3 induction differs from the observation by Seo et al (2000a) that dehydration (i.e., in air flow hood for 3 hr) significantly induced AAO3 expression in Arabidopsis shoot. The reason for this discrepancy is probably because our stress condition (dehydration in still air for approximately 40 min to lose 20% fresh weight, followed by incubation at 100% humidity for 3 or 6 hr) was not as severe. Our result implies that LOS5/ABA3 may be the key regulator in this last step of ABA biosynthesis. Consistent with this speculation, Sagi et al. (1999) found that sulfuration with $Na_2S$ 'superinduced' the activity of AO and XDH in wild type tomato crude extracts, suggesting that MoCo sulfuration limits AB-aldehyde oxidase activity. ABA up-regulation of LOS5/ABA3 expression (FIGS. 9C and 9D) is very intriguing and may suggest a positive feedback regulation of ABA biosynthesis by ABA.

The availability of plant mutants defective in ABA biosynthesis has provided an excellent opportunity to study gene regulation by ABA under various abiotic stress conditions. In doing so, most researchers have used aba1 or abi1 and abi2 along with the respective wild types. The Arabidopsis ABA deficient mutant aba1 was the first mutant defective in ABA biosynthesis isolated in Arabidopsis (Koornneef et al., 1982). Recently, additional ABA deficient Arabidopsis mutants, aba2 and aba3, became available (Léon-Kloosterziel et al., 1996). However, stress gene regulation in these recently isolated mutants has not been reported.

Extensive studies with aba1 or abi1/2 mutants have yielded considerable, yet, sometimes conflicting information. For example, whereas Savoure et al. (1997) reported that the expression of P5CS genes is independent of ABA since they observed that the expression level is similar in wild type and in aba1 under cold or drought treatments. They suggested that ABA might affect proline biosynthesis post-transcriptionally (Savoure et al., 1997). On the other hand, Yoshiba et al. (1999) reported that AtP5CS1 induction by drought and salt stress is regulated both by ABA-dependent and ABA-independent pathways. Furthermore, Strizhov et al. (1997) found that stress-induced P5CS1 gene expression absolutely requires ABA, which is consistent with our findings here (FIG. 2). To help clear the confusion, several reviews have been published and some consensuses have been reached (Leung and Giraudat, 1998; Shinozaki and Yamaguichi-Shinozaki, 1997; Thomashow, 1999; Rock, 2000). Although low temperature treatment can trigger a transient increase in ABA and application of ABA can induce the expression of cold-responsive genes at warm temperatures and increases plant freezing tolerance, a general consensus is that ABA does not have an important role in regulating the expression of the DRE/CRT class of genes (Thomashow, 1999). In the present study, we found that los5-1 seedlings show a dramatic reduction in the expression of the RD29A-LUC transgene under low temperature treatment (FIGS. 1B and 1G). RNA blot analysis showed that the induction of COR15, KIN1, COR47, RD29A, RAB18, and ADH by low temperature is also significantly reduced in los5-1 mutant plants (FIGS. 2 and 9D). The reduction in cold-regulated gene expression as seen in los5-1 was, however, not observed in aba1-1 (FIG. 10D). In fact, cold-induction of both ADH and RD29A was enhanced in aba1-1 (FIG. 10D). Similarly, cold induction of RD29A-LUC expression was enhanced in los6/aba1 mutant seedlings (FIG. 6B). Our results with los6/aba1 are consistent with previous studies on cold regulated gene expression carried out with aba1-1 (reviewed in Thomashow, 1999). The different effects of los5 and aba1 mutations raise the question whether the significant role played in cold-regulated gene expression by LOS5/ABA3 is a result of ABA-deficiency. This was partially addressed by our experiment as shown in FIG. 6B: whereas treatment with ABA complemented los6/aba1 defect in cold-regulated RD29A-LUC expression, the same treatment failed to rescue los5/aba3 (FIG. 6B). This suggests that in addition to its role in ABA biosynthesis, LOS5/ABA3 may have additional roles in cold regulation. Consistent with this notion is the finding that although exogenous ABA achieves similar or slightly higher expression of COR47, RD22, RD29A, and ADH (FIGS. 2, 6, and 9D) in los5 relative to that in the wild type, ABA fails to induce the expression of COR15 and P5CS, and has a reduced induction of KIN1 (FIG. 2). These results strongly suggest that cold signaling requires a function of LOS5/ABA3 that is not directly related to ABA biosynthesis. Presently, it is unclear how LOS5/ABA3 is involved in cold or ABA regulation of some genes.

In contrast to low temperature, drought stress can dramatically stimulate de novo ABA biosynthesis and thus ABA is more closely involved in drought/salt stress responses (Ingram and Bartels, 1996; Bray, 1993). Gene regulation by drought has been thought to involve both ABA-dependent and ABA-independent pathways (Shinozaki and Yamaguchi-Shinozaki, 1997). Because genes such as RD29A, KIN1, and COR47 have both ABRE complex and the DRE/CRT elements, presumably, they can be activated by abiotic stress alone in the absence of ABA. Analysis using aba1 or abi mutants indeed showed that this is likely the case (Thomashow, 1999; Shinozaki and Yamaguchi-Shinozaki, 1997). However, our results with los5 mutants clearly present a quite different picture. Under osmotic stress, the expression of RD29A-LUC is almost abolished in los5 (FIGS. 1F and 1G). RNA blot analyses also found that the los5 mutation virtually blocks the induction of COR15, KIN1, RD22, P5CS, and RAB18 by salt and drought (PEG) stress (FIGS. 2 and 9D), and it severely impairs the induction of RD29A, COR47, and ADH by the stresses (FIGS. 2 and 9D). To ascertain whether the effect of los5 on osmotic stress-regulated gene expression is accounted for by ABA deficiency, we applied ABA together with salt stress and analyzed RD29A-LUC expression. The result indicates that ABA restores the RD29A-LUC expression to the wild type levels both in los5-1 and in los6/aba1 (FIG. 6A). Our previous RNA blot analysis with the wild type plants showed that under this treatment condition, the RD29A-LUC luminescence expression faithfully mirrors the pattern of endogenous RD29A expression (Xiong et al., 1999b). These results suggest that the observed defects in salt/drought-regulated gene expression in los5 mutant plants are most likely a consequence of ABA deficiency. Currently, an alternative possibility that LOS5 may have yet unknown roles that are not related to ABA biosynthesis in regulating 'ABA-independent' osmotic stress signaling cannot be completely ruled out. This is because the reduced magnitude of gene induction by drought or salt in aba1/los6 was not as dramatic as in los5 (FIG. 6A), although these mutants show a similar extent of ABA deficiency by bulk quantitative measurement.

The los5 mutation seems to have little effect on salt stress-regulated DREB2A expression (FIG. 10E). This raises the possibility that DREB2A function may require ABA-dependent factor(s) to activate downstream gene expression. Previously, our genetic analysis using RD29A-LUC as a molecular marker has shown that ABA-dependent and ABA-independent signaling pathways may not function independently of each other. Rather, there exists extensive connections or 'crosstalk' between them (Ishitani et al., 1997; Xiong et al., 1999a). The present molecular characterization of los5 mutants further casts doubt on the ABA-independency of 'ABA-independent' stress signal transduction pathways, at least as far as the DRE/CRT genes are concerned. Furthermore, it has been shown that ectopic expression of DREB2A alone does not activate downstream gene expression (Liu et al., 1998). As has been suggested by Liu et al. (1998), DREB2A activity in activating stress-responsive genes may require posttranscriptional modifications. Thus, it is possible that phosphorylation/dephosphorylation of DREB2A or the functions of its co-factors may be dependent on ABA-regulated molecules such as ABI1, ABI2, CDPKs, or numerous other ABA-responsive regulatory factors (e.g., Leung et al., 1997; Leung and Giraudat, 1998; Finkelstein and Lynch, 2000; Rock, 2000; Merlot et al., 2001). This interdependency of ABA and stress signaling may underlie the mechanisms for synergistic effect of ABA and drought/salt stress on the regulation of stress-responsive genes as observed in the present study (FIG. 6A) and elsewhere (Bostock and Quatrano, 1992; Xiong et al., 1999b).

EXAMPLES

Having generally described this invention, a further understanding can be obtained by reference to certain specific examples which are provided herein for purposes of illustration only and are not intended to be limiting unless otherwise specified.

Example 1

Characterization of the LOS5/ABA3 Locus

Isolation of los5 Mutants

*Arabidopsis thaliana* (C24 ecotype) expressing the RD29A-LUC transgene (referred to as the wild type) were obtained by *Agrobacterium*-mediated transformation (Ishitani et al., 1997). Seeds of wild type RD29A-LUC were mutagenized by ethyl methanesulfonate (Ishitani et al., 1997). $M_2$ were planted on 0.6% agar plates containing full strength Murashige and Skoog salt base (MS salt base; JRH Biosceicnes, Lenex, Kans.) and were germinated and grown at 22±2° C. under continuous white light. One-week-old seedlings were screened for mutants with altered RD29A-LUC (i.e. luminescence) expression in response to low temperature, ABA, or osmotic stress using a thermoelectrically cooled CCD camera. For luminescence imaging, plants were sprayed with 1 mM luciferin in 0.01% Triton X-100 and then kept in the dark for 5 min before imaging. All images were acquired with a 5 min exposure time. The luminescence intensity of each seedling was quantified with the WinView software.

Stress and ABA Treatment

For ABA treatment, 100 µM (±)-cis, trans-abscisic acid in $H_2O$ was sprayed uniformly on leaves of seedlings and the plants were incubated at room temperature under cool-white light for 4 hr (for luminescence imaging) or 3 hr (for RNA analysis). For NaCl or PEG treatment, seedlings on MS plates were transferred to filter paper saturated with MS solution supplemented with 300 mM NaCl or 30% of polyethylene glycol (molecular weight 6,000) and incubated for 5 hr. Unless otherwise stated, cold treatment for image analysis and RNA analysis were done by incubating seedlings growing in plates at 0° C. in the dark for 48 hr (for imaging) or 12 hr (for RNA analysis). Because longer treatment at −5 or −10° C. will result in freezing of the agar media, these freezing temperature treatments only lasted for 3 hr. After the treatment, the plates were placed at room temperature for 2 hr to thaw before luminescence images acquisition. For ABA plus NaCl treatment, seedlings were transferred onto a filter paper saturated with 300 mM NaCl in MS solution and sprayed immediately with 100 µM ABA. The plants were then incubated under cool-white light for 4 hr before luciferase imaging. For low temperature plus ABA treatment, seedlings on agar plates were briefly incubated at 0±1° C. for 10 min and then sprayed with 100 µM ABA and incubated in the dark at 0±1° C. for 48 hr before image analysis.

Genetic Analysis of los5 Mutants and Map-based Cloning of LOS5

For genetic analysis, the los5 mutants were crossed to the wild type and other mutants we isolated with similar luminescence phenotypes. The $F_1$ and $F_2$ seedlings were subjected to luminescence analysis and scored for los5 luminescence phenotypes. los5-1 was also crossed with aba1, aba2, and aba3 mutants (obtained from Arabidopsis Biological Resource Center, Columbus, Ohio). Part of the resulting $F_1$ and $F_2$ seedlings was treated with 300 mM NaCl for luminescence image analysis and part was directly planted in soil for scoring wilty phenotypes under reduced humidity. For genetic mapping of the los5 mutation, los5-1 mutant in the C24 ecotype was crossed with wild type plants of the Columbia ecotype. The resulting $F_1$ plants were allowed to self and homozygous los5-1 mutants in the segregating F$_2$ population were selected based on their reduced luminescence when cold-treated and a control treatment with ABA were used to rule out those that did not have the RD29A-LUC transgene. A part of the seedlings were also tested for their reduced luminescence under NaCl treatment. Mapping of LOS5 was carried out as described previously (Lee et al., 2001). SSLP markers were developed by surveying released genomic DNA sequences for simple repeats using the RepeatMasker program (http://ftp.genome.washington.edu/cgi-bin/RepeatMasker). Primer pairs flanking these simple repeats that generate PCR products with size polymorphisms on 4% agarose gels between the C24 and Columbia ecotypes were used as molecular markers for mapping.

RNA Analysis

Ten-day-old seedlings on MS agar plates were treated were treated with cold, ABA, NaCl, or PEG as described in the above section. For drought treatment, seedlings at rosette stage in potted soil was detached from soil surface and allowed to lose 20% of their fresh weight. The dehydrated materials were then incubated in a container with 100% relative humidity for 3 hr or 6 hr before being frozen in liquid N$_2$ for RNA extraction. Total RNA from control or treated plants was extracted and analyzed as described (Ishitani et al., 1998). Gene-specific probes were as described (Ishitani et al., 1998; Lee et al., 2001).

Stress Tolerance Assays

For freezing sensitivity assay, wild type and los5 seedlings growing in potted soil in a growth chamber (22±2° C., 16 hr light and 8 hr dark) for 3 weeks were first incubated at 4° C. in the light for 48 hr to cold-acclimate. After this cold acclimation, the plants were subjected to freezing at −7° C. for 5 hr. Upon finishing the treatment, plants were immediately transferred to 4° C. under white light and were incubated overnight. In the following morning the plants were placed into a growth chamber. Seedling damage was scored at times as indicated in the text.

For NaCl tolerance tests, 7-day-old seedlings of los5-1 and wild type growing on MS plates (solidified with 1.2% agar) were transferred to MS agar plates supplemented with different concentrations of NaCl. The plates were then placed vertically at 22±2° C. under white light and root elongation was measured daily for up to 10 days. To measure ion leakage in seedlings induced by PEG treatment, one-week-old wild type and los5-1 seedlings growing in MS agar plates were carefully removed from the plate, briefly rinsed in distilled water and placed in solutions containing 30% of polyethylene glycol (PEG) (mw 6,000) for 5 hr. After the treatment, seedlings were rinsed briefly in distilled water and immediately placed in a tube with 5 ml H$_2$O. The tube was then gently agitated for 3 hr before the electrolyte content was measured. Four replicates of each treatment were conducted.

Water Loss Measurements

For water loss measurement, plants at the rosette stage were detached from soil surface and weighed immediately in a plastic weighing boat. The boat with the plants was then placed on laboratory bench (relative humidity ~30%) and weighed at designated time intervals. There were four replicates for each line. Percent loss of fresh weight was calculated based on the initial weight of the plants.

Proline Assays

One-week-old seedlings of los5-1 and wild type grown in MS agar plate were sprayed with 50 μM ABA or transferred on to filter paper in a petri dish saturated with 150 mM NaCl and incubated at 22±2° C. under white light for 24 hr. After the treatment, the samples were frozen in liquid nitrogen and kept at −80° C. for proline assay. Proline concentration was determined as described by Bates et al. (1973).

ABA Measurement

Rosette leaves were excised from 3-week-old mutant and wild type plants grown in soil and placed on lab bench. After the leaves lost 30% of initial fresh weight (over a period of approximately 2 hrs), they were placed in a sealed plastic bag with wet paper towels for an additional 5 hrs. Unstressed control leaves were placed directly in a high humidity sealed plastic bag without losing fresh weight. The tissues were then frozen in liquid nitrogen and ground into powder. One gram of the tissues was suspended in 15 mL of extraction solution containing 80% methanol, 100 mg/L butylated hydroxytoluene and 0.5 g/L citric acid monohydrate. The suspension was stirred overnight at 4° C. and centrifuged at 1,000 g for 20 min. The supernatant was transferred to a new tube and dried under vacuum. The dry residue was dissolved with 100 μL of methanol plus 900 μL of tris-buffered saline (50 mM Tris, 0.1 mM MgCl$_2$.6H$_2$O, 0.15 M NaCl, pH 7.8). ABA concentration in the solution was then determined using the Phytodetek ABA immunoassay kit (Idetek, Inc., Sunnyvale, Calif.).

Example 2

Overexpression of the LOS5 Gene Increases Plant Tolerance to Drought Stress

Since loss of function mutations in the LOS5 gene resulted in de-regulated expression of stress-responsive genes and increased sensitivity to drought and salt stress, it was hypothesized that increased expression of LOS5 might affect gene expression pattern under stress and increase plant drought tolerance.

To test this possibility, LOS5 full length cDNA was transcriptionally fused to the CaMV 35S promoter and a transcriptional enhancer. The insert was cloned into the binary vector pCAMBIA1200. The resulting plasmid was transferred into Arabidopsis ecotypes Columbia and C24 (containing the RD29A-LUC reporter gene), respectively. Around 70 transformants were selected in each ecotype background for further tests. To examine the impact of overexpressing LOS5 gene on stress gene regulation and plant water relations, seedlings of transgenic plants were assayed for 1) their expression of the RD29A-LUC transgene under salt stress treatment; 2) their transpiration rates by measuring water loss rate of detached leaves, and 3) drought tolerance in soil growing plants.

The results with 7 lines in the C24 background indicated that upon treatment with 300 mM NaCl, the expression level for the RD29A-LUC reporter gene in LOS5-overexpressing line is 39 to 96 percent higher than in the wild type plants. During a 4-hr period, the water transpiration rate from detached leaves of LOS5-overexpressing plants is significantly lower than that in the wild type plants in three lines tested. This reduced transpiration can also be seen when detached leaves were let to dry at the room condition (see FIG. 12). The reduced transpiration will significantly increase drought tolerance of the plants.

REFERENCES

Akaba, S., Leydecker, M. T., Moureaux, T., Oritani, T., and Koshiba, T. (1998). Aldehyde oxidase in wild type and aba1 mutant leaves of *Nictotiana plumbaginifolia*. Plant Cell Physiol. 39, 1281–1286.

Amrani, L., Cecchetto, G., Scazzocchio, C., and Glatigny, A. (1999). The hxB gene, necessary for the post-translational activation of purine hydroxylases in *Aspergillus nidulans*, is independently controlled by the purine utilization and the nicotinate utilization transcriptional activating systems. Mol. Microbiol. 31, 1065–1073.

Bostock, R. M., and Quatrano, R. S. (1992). Regulation of Em gene expression in rice, interaction between osmotic stress and abscisic acid. Plant Physiol 98, 1356–1363.

Bray, E. A. (1993). Molecular responses to water deficit. Plant Physiol. 103, 1035–1040.

Bates, L. S. (1973). Rapid determination of free proline for water-stress studies. Plant Soil. 39, 205–207.

Cutler, A. J., and Krochko, J. E. (1999). Formation and breakdown of ABA. Trends Plant Sci. 4, 472–478.

Finkelstein, R. R., and Lynch, T. J. (2000). The Arabidopsis abscisic acid response gene ABI5 encodes a basic leucine zipper transcriptional factor. Plant Cell 12, 599–609.

Fujii, T., Maeda, M., Mihara, H., Kurihara, T., Esaki, N., and Hata, Y. (2000). Stucture of a NifS homologue: X-ray structure analysis of CsdB, an *Escherichia coli* counterpart of mammalian selenocysteine lyase. Biochemistry. 39, 1263–1273.

Gilmour, S. J., Artus, N. N., and Thomashow, M. F. (1992). cDNA sequence analysis and expression of two cold-regulated genes of *Arabidopsis thaliana*. Plant Mol. Biol. 18, 13–32.

Guiltinan, M. J., Marcotte, W. R., and Quatrano, R. S. (1990). A plant leucine zipper protein that recognizes an abscisic acid response element. Science 250, 267–271.

Hasegawa, P. M., Bressan, R. A., Zhu, J. K., and Bohnert, H. J. (2000). Plant cellular and molecular responses to high salinity. Annu. Rev. Plant Physiol. Plant Mol. Biol. 51, 463–499.

Hilleren, P., and Parker, R. (1999). Mechanisms of mRNA surveillance in eukaryotes. Annu. Rev. Genet. 33, 229–260.

Hong, Z., Lakkineni, K., Zhang, Z., and Verma, D. P. S. (2000). Removal of feedback inhibition of $\Delta^1$-pyrroline-5-carboxylate synthase results in increased proline accumulation and protection of plants from osmotic stress. Plant Physiol. 122, 1129–1136.

Ingram, J., and Bartel, D. (1996). The molecular basis of dehydration tolerance in plants. Annu. Rev. Plant Physiol. Plant Mol. Biol. 47, 377–403.

Ishitani, M., Xiong, L., Lee, H., Stevenson, B., and Zhu, J. K. (1998). HOS1, a genetic locus involved in cold-responsive gene expression in *Arabidopsis*. Plant Cell 10, 1151–1161.

Ishitani, M., Xiong, L., Stevenson, B., and Zhu, J.-K. (1997). Genetic analysis of osmotic and cold stress signal transduction in *Arabidopsis:* Interactions and convergence of abscisic acid-dependent and abscisic acid-independent pathways. Plant Cell 9, 1935–1949.

Iuchi, S., Kobayashi, M., Yamaguchi-Shinozaki, K., and Shinozaki, K. (2000). A stress-inducible gene for 9-cis-epoxycarotenoid dioxygenase involved in abscisic acid biosynthesis under water stress in drought-tolerant cowpea. Plant Physiol. 123, 553–562.

Kaiser, J. T., Clausen, T., Bourenkow, G. P., Bartunik, H.-D., Steinbacher, S., and Huber, R. (2000). Crystal structure of a NifS-like protein from *Thermotoga maritime:* Implications for iron sulphur cluster assembly. J. Mol. Biol. 297, 451–464.

Kisher, C., Schindelin, H., and Rees, D.C. (1997). Molybdenum-cofactor-containing enzymes: structure and mechanism. Annu. Rev. Biochem. 66, 233–267.

Koornneef, M., Jorna, M. L., Brinkhorst-van der Swan, D. L. C., and Karssen, C. M. (1982). The isolation of abscisic acid deficient mutants by selection of induced revertants in non-germinating gibberellin sensitive lines of *Arabidopsis thaliana*. Theor. Appl. Genet. 61, 385–393.

Koornneef, M., Léon-Kloosterziel, K. M., Schwartz, S. H., and Zeevaart, J. A. D. (1998). The genetic and molecular dissection of abscisic acid biosynthesis and signal transduction in *Arabidopsis*. Plant Physiol. Biochem. 36, 83–89.

Koornneef, M., Reuling, G., and Karssen, C. M. (1984). The isolation and characterization of abscisic acid insensitive mutants of *Arabidopsis thaliana*. Physiol. Plant. 61, 377–383.

Kurkela, S. and Franck, M. (1990). Cloning and characterization of a cold- and ABA-inducible *Arabidopsis* gene. Plant Mol. Biol. 15, 137–144.

Lee, H., Xiong, L., Gong, Z., Ishitani, M., Stevenson, B., and Zhu, J.-K. (2001). The Arabidopsis HOS1 gene negatively regulates cold signal transduction and encodes a RING finger protein that displays cold-regulated nucleo-cytoplasmic partitioning. Genes Dev. 15, 912–924.

Léon-Kloosterzie, K. M., Gil, M. A., Ruijs, G. J., Jacobsen, S. E., Olszewski, N. E., Schwart, S. H., Zeevaart, J. A., and Koornneef, M. (1996). Isolation and characterization of abscisic acid-deficient *Arabidopsis* mutants at two new loci. Plant J. 10, 655–661.

Leung, J., and Giraudat, J. (1998). Abscisic acid signal transduction. Annu. Rev. Plant Physiol. Plant Mol. Biol. 49, 199–222.

Leung, J., Merlot, S., and Giraudat, J. (1997). The *Arabidopsis* ABSCISIC ACID-INSENSITIVE 2 (ABI2) and ABI1 genes encode homologous protein phosphatase 2C involved in abscisic acid signal transduction. Plant Cell 9, 759–771.

Leydecker, M. T., Moureaux, T., Kraepiel, Y., Schnorr, K., and Caboche, M. (1995). Molybdenum cofactor mutants, specifically impaired in xanthine dehydrogenase activity and abscisic acid biosynthesis, simultaneously overexpress nitrate reductase. Plant Physiol. 107, 1427–1431.

Lin, C., and Thomashow, M. F. (1992). DNA sequence analysis of a complementary DNA for cold-regulated *Arabidopsis* gene cor15 and characterization of the COR15 polypeptide. Plant Physiol. 99, 519–525.

Liu, Q., Kasuga, M., Sakuma, Y., Abe, H., Miura, S., Yamaguchi-Shinozaki, K., and Shinozaki, K. (1998). Two transcription factors, DREB1 and DREB2, with an EREBP/AP2 DNA binding domain separate two cellular signal transduction pathways in drought- and low-temperature-responsive gene expression, respectively, in Arabidopsis. Plant Cell 10, 1391–1406.

Liotenberg, S., North, H., and Marion-Poll, A. (1999). Molecular biology and regulation of abscisic acid biosynthesis in plants. Plant Physiol. Biochem. 37, 341–350.

Llorente, F., Oliveros, J. C., Martinez-Zapater, J. M., and Salinas, J. (2000). A freezing-sensitive mutant of Arabidopsis, frs1, is a new aba3 allele. Planta 211, 648–655.

Marin, E., Nussaume, L., Quesada, A., Gonneau, M., Sotta, B., Hugueney, P., Frey, A., and Marion-Poll, A. (1996). Molecular identification of zeaxanthin epoxidase of *Nicotiana plumbaginifolia*, a gene involved in abscisic acid biosynthesis and corresponding to the ABA locus of *Arabidopsis thaliana*. EMBO. J. 15, 2331–2342.

Marin, E., and Marion-Poll, A. (1997). Tomato flacca mutant is impaired in ABA aldehyde oxidase and xanthine dehydrogenase activities. Plant Physiol. Biochem. 35, 369–372.

McCourt, P. (1999). Genetic analysis of hormone signaling. Ann. Rev. Plant Physiol. Plant Mol. Biol. 50, 219–243.

Mendel, R. R., and Schwarz, G. (1999). Molybdoenzymes and molybdenum cofactor in plants. Crit. Rev. Plant Sci. 18, 33–69.

Merlot, S., Costi, F., Guerrier, D., Vavasseur, A., and Giraudat, J. (2001). The ABI1 and ABI2 protein phosphatases 2C act in a negative feedback regulatory loop of the abscisic acid signalling pathway. Plant J. 25, 295–603.

Qin, X., and Zeevaart, J. A. D. (1999). The 9-cis-epoxycarotenoid cleavage reaction is the key regulatory step of abscisic acid biosynthesis in water-stressed bean. Proc. Natl. Acad. Sci. USA 96, 15354–15361.

Rajagoplant, K. V. (1991). Novel aspects of the biochemistry of the molybdenum cofactor. Adv Enzymol. 64, 215–90.

Reiss, J. (2000). Genetics of molybdenum cofactor deficiency. Human Genetics 106, 157–163.

Rock, C. D. (2000). Pathways to abscisic acid-regulated gene expression. New Phytol. 148, 357–396.

Rock, C. D., and Zeevaart, J. A. D. (1991). The aba mutant of *Arabidopsis thaliana* is impaired in epoxy-carotenoid biosynthesis. Proc. Natl. Acad. Sci. USA. 88, 7496–7499.

Roosens, N. H., Willem, R., Li, Y., Verbruggen, I., Biesemans, M., and Jacobs, M. (1999). Proline metabolism in the wild-type and in a salt-tolerant mutant of *Nicotiana plumbaginifolia* studied by $^{13}$C-nuclear magnetic resonance imaging. Plant Physiol 121, 1281–1290.

Sagi, M., Fluhr, R., and Lips, S. H. (1999). Aldehyde oxidase and xanthine dehydrogenase in a flacca tomato mutant with deficient abscisic acid and wilty phenotype. Plant Physiol. 120, 571–577.

Savoure, A., Hua, X.-J., Bertauche, N., Van-Montagu, M. and Verbruggen, N. (1997). Abscisic acid-independent and abscisic acid dependent regulation of proline biosynthesis following cold and osmotic stresses in *Arabidopsis thaliana*. Mol. Gen. Genet. 254, 104–109.

Scazzocchio, C. (1973). The genetic control of molybdoflavoproteins in *Aspergillus nidulans*. Use of the NADH dehydrogenase activity associated with xanthine dehydrogenase to investigate substrate and production induction. Mol. Gen. Genet. 125, 147–155.

Schwatz, S. H., Léon-Kloosterzie, K. M., Koornneerf, M., and Zeevaart, J. A. D. (1997a). Biochemical characterization of the aba2 and aba3 mutants in *Arabidopsis thaliana*. Plant Physiol. 114, 161–166.

Schwartz, S. H., Tan, B. C., Gage, D. A., Zeevaart, J. A. D., and McCarty, D. R. (1997b). Specific oxidative cleavage of carotenoid by VP14 of maize. Science 276, 1872–1874.

Seo, M., Koiwa, H., Akaba, S., Komano, T., Oritani, T., Kamiya, Y., and Koshiba T. (2000a). Abscisic acid aldehyde oxidase of *Arabidopsis thaliana*. Plant J. 23, 481–488.

Seo, M., Peeters, A. J. M., Koiwai, H., Oritani, T., Marion-Poll, A., Zeevaart, J. A. D., Koornneef, M., Kamiya, Y., and Koshiba, T. (2000b). The Arabidopsis aldehyde oxidase 3 (AAO3) gene product catalyzes the final step in abseisic acid biosynthesis in leaves. Proc. Natl. Acad. Sci. USA 97, 12908–12913.

Shen, Q., and Ho, T. H. D. (1995). Functional dissection of an abscisic acid (ABA)-inducible gene reveals two independent ABA-responsive complexes each containing a G-box and a novel cis-acting element. Plant Cell 7, 295–307.

Shinozaki, K., and Yamaguchi-Shinozaki, K. (1997). Gene expression and signal transduction in water-stress response. Plant Physiol. 115, 327–334.

Stockinger, E. J., Gilmour, S. J., and Thomashow, M. F. (1997). *Arabidopsis thaliana* CBF1 encodes an AP2 domain-containing transcriptional activator that binds to the C-repeat/DRE, a cis-acting DNA regulatory element that stimulates transcription in response to low temperature and water deficit. Proc. Natl. Acad. Sci. USA 94, 1035–1040.

Strizhov, N., Abraham, E., Okresz, L., Blickling, S., Zilberstein, A., Schell, J., Koncz, C., and Szabados, L. (1997). Differential expression of two P5CS genes controlling proline accumulation during salt-stress requires ABA and is regulated by ABA1, ABI1 and AXR2 in *Arabidopsis*. Plant J. 12, 557–569.

Tan, B. C., Schwartz, S. H., Zeevaart, J. A. D., and McCarty, D. R. (1997). Genetic control of abscisic acid biosynthesis in maize. Proc. Natl. Acad. Sci. USA 94, 12235–12240.

Taylor, I. B., Burbidage, A., and Thompson, A. J. (2000). Control of abscisic acid synthesis. J. Exp. Bot. 51, 1563–1574.

Thomashow, M. F. (1999). Plant cold acclimation: freezing tolerance genes and regulatory mechanisms. Annu. Rev. Plant Physiol. Plant Mol. Biol. 50, 571–599.

Thompson, A. J., Jackson, A. C., Symonds, R. C., Mulholland, B. J., Dadswell, A. R., Blake, P. S., Burbidge, A., and Taylor, I. B. (2000). Ectopic expression of a tomato 9-cis-epoxycarotenoid dioxygenase gene causes over-production of abscisic acid. Plant J. 23, 363–374.

Vasil, V., Marcotte, W. R. Jr., Rosenkrans, L., Cocciolone, S. M., Vasil, I. K., Quatrano, R. S., and McCarty, D. R. (1995). Overlap of Viviparous1 (Vp1) and abscisic acid response elements in the Em promoter: G-box elements are sufficient but not necessary for VP1 transactivation. Plant Cell 7, 1511–1518.

Wahl, R., Warner, C. K., Finnerty, V., and Rajagopalan, K. (1982). *Drosophila melanogaster* ma-l mutants are defective in the sulfuration of desulfo Mo hydroxylases. J. Biol. Chem. 257, 3958–3962.

Watanabe, T., Ihara, N., Itoh, T., Fujita, T., and Sugimoto, Y. (2000). Deletion mutation in *Drosphila* ma-l homologous, putative molybodopterin cofactor sulfurase gene is associated with bovine xanthinuria Type II. J. Biol. Chem. 275, 21789–21792.

Xin, Z., and Browse, J. (1998). eskimo1 mutants of *Arabidopsis* are constitutively freezing-tolerant. Proc. Natl. Acad. Sci. USA 95, 7799–7804.

Xiong, L., Ishitani, M., Lee, H., and Zhu, J. K. (1999a). HOS5-a negative regulator of osmotic stress-induced gene expression in *Arabidopsis thaliana*. Plant J. 19, 569–578.

Xiong, L., Ishitani, M., and Zhu, J. K. (1999b). Interaction of osmotic stress, temperature, and abscisic acid in the regulation of gene expression in *Arabidopsis*. Plant Physiol. 119, 205–211.

Yamaguchi-Shinozaki, K., Koizumi, M., Urao, S., and Shinozaki, K. (1992). Molecular cloning and characterization of 9 cDNAs for genes that are responsive to desiccation in *Arabidopsis thaliana*: sequence analysis of one cDNA clone that encodes a putative transmembrane channel protein. Plant Cell Physiol. 33, 217–224.

Yamaguchi-Shinozaki, K., and Shinozaki, K. (1994). A novel cis-acting element in an Arabidopsis gene is involved in responsiveness to drought, low-temperature, or high-salt stress. Plant Cell 6, 251–264.

Yoshiba, Y., Nanjo, T., Miura, S., Yamaguchi-Shinozaki, K., and Shinozaki, K. (1999). Stress-responsive and developmental regulation of $\Delta^1$-pyrroline-5-carboxylate synthetase 1 (P5CS1) gene expression in *Arabidopsis thaliana*. Biochem. Biophys. Res. Comm. 261, 766–772.

Zheng, L., White, R. H., Cash, V. L., Jack, R. F., and Dean, D. R. (1993). Cysteine desulfurase activity indicates a role for NifS in metallocluster biosynthesis. Proc. Natl. Acad. Sci. USA 90, 2754–2758.

Zhu, J. K., Hasegawa, P. M., and Bressan, R. A. (1997). Molecular aspects of osmotic stress in plants. Crit. Rev. Plant Sci. 16, 253–277.

Obviously, numerous modifications and variations of the present invention are possible in light of the above teachings. It is therefore to be understood that within the scope of the appended claims, the invention may be practiced otherwise than as specifically described herein.

The content of Xiong et al., The Plant Cell, Volume 13, September 2001, pp. 2063–2083, is incorporated herein by reference in its entirety.

The invention claimed is:

1. A plant transformed with a nucleic acid encoding a molybdenum cofactor sulfurase, wherein said molybdenum cofactor sulfurase has a homology of at least 95% with SEQ ID NO: 2.

2. The transformed plant of claim 1, wherein the plants have increased drought tolerance.

3. The transformed plant of claim 1, wherein the plants have increased salt tolerance.

4. The transformed plant of claim 1, wherein the plants have increased freezing tolerance.

5. The transformed plant of claim 1, wherein the molybdenum cofactor sulfurase has the amino acid sequence of SEQ ID NO: 2.

6. The transformed plant of claim 1, wherein the molybdenum cofactor sulfurase is encoded by a nucleic acid having the sequence of SEQ ID NO: 1.

7. The transformed plant of claim 1, wherein the molybdenum cofactor sulfurase is encoded by a nucleic acid which hybridizes under stringent conditions to the complement of SEQ ID NO: 1, wherein said stringent conditions comprise washing in 5×SSC at a temperature of from 50 to 68° C.

8. The transformed plant of claim 1, wherein the plant is *Arabidopsis thalania*.

9. The transformed plant of claim 1, wherein the plant is selected from the group consisting of wheat, corn, peanut cotton, oat, and soybean.

10. A method for preparing the transformed plant of claim 1, comprising transforming the plant with a nucleic acid encoding said molybdenum cofactor sulfurase.

11. A plant cell, transformed with a nucleic acid encoding a molybdenum cofactor sulfurase, wherein said molybdenum cofactor sulfurase has a homology of at least 95% with SEO ID NO: 2.

12. The transformed plant cell of claim 11 wherein the plants have increased drought tolerance.

13. The transformed plant cell of claim 11, wherein the plants have increased salt tolerance.

14. The transformed plant cell of claim 11, wherein the plants have increased freezing tolerance.

15. The transformed plant cell of claim 11, wherein the molybdenum cofactor sulfurase has the amino acid sequence of SEQ ID NO: 2.

16. The transformed plant cell of claim 11, wherein the molybdenum cofactor sulfurase is encoded by a nucleic acid having the sequence of SEQ ID NO: 1.

17. The transformed plant cell of claim 11, wherein the molybdenum cofactor sulfurase is encoded by a nucleic acid which hybridizes under stringent conditions to the complement of SEQ ID NO: 1, wherein said stringent conditions comprise washing in 5×SSC at a temperature of from 50 to 68° C.

18. The transformed plant cell of claim 11, wherein the plant is *Arabidopsis thalania*.

19. The transformed plant cell of claim 11, wherein the plant is selected from the group consisting of wheat, corn, peanut cotton, oat, and soybean.

20. A method of preparing the transformed plant cell of claim 11, comprising transforming the cell with a nucleic acid encoding said molybdenum cofactor sulfurase.

21. A method of overexpressing a molybdenum cofactor sulfurase in a plant, comprising transforming the plant with a vector which encodes a molybdenum cofactor sulfurase, wherein said molybdenum cofactor sulfurase has a homology of at least 95% with SEQ ID NO: 2.

22. The method of claim 21, wherein the plants have increased drought tolerance.

23. The method of claim 21, wherein the plants have increased salt tolerance.

24. The method of claim 21, wherein the plants have increased freezing tolerance.

25. The method of claim 21, wherein the molybdenum cofactor sulfurase has the amino acid sequence of SEQ ID NO: 2.

26. The method of claim 21, wherein the molybdenum cofactor sulfurase is encoded by a nucleic acid having the sequence of SEQ ID NO: 1.

27. The method of claim 21, wherein the molybdenum cofactor sulfurase is encoded by a nucleic acid which hybridizes under stringent conditions to the complement of SEQ ID NO: 1, wherein said stringent conditions comprise washing in 5×SSC at a temperature of from 50 to 68° C.

28. The method of claim 21, wherein the plant is *Arabidopsis thalania*.

29. The method of claim 21, wherein the plant is selected from the group consisting of wheat, corn, peanut cotton, oat, and soybean.

30. A method of overexpressing a molybdenum cofactor sulfurase in a plant cell, comprising transforming the plant cell with a vector which encodes a molybdenum cofactor sulfurase, wherein said molybdenum cofactor sulfurase has a homology of at least 95% with SEQ ID NO: 2.

31. The method of claim 30, wherein the plants have increased drought tolerance.

32. The method of claim 30, wherein the plants have increased salt tolerance.

33. The method of claim 30, wherein the plants have increased freezing tolerance.

34. The method of claim 30, wherein the molybdenum cofactor sulfurase has the amino acid sequence of SEQ ID NO: 2.

35. The method of claim 30, wherein the molybdenum cofactor sulfurase is encoded by a nucleic acid having the sequence of SEQ ID NO: 1.

36. The method of claim 30, wherein the molybdenum cofactor sulfurase is encoded by a nucleic acid which hybridizes under stringent conditions to the complement of SEQ ID NO: 1, wherein said stringent conditions comprise washing in 5×SSC at a temperature of from 50 to 68° C.

37. The method of claim 30, wherein the plant cell is *Arabidopsis thalania*.

38. The method of claim 30, wherein the plant cell is selected from the group consisting of wheat, corn, peanut cotton, oat, and soybean.

39. The transformed plant of claim 1, wherein the nucleic acid also comprises a promoter inducible in the plant.

40. The plant cell of claim 11, wherein the nucleic acid also comprises a promoter inducible in the plant cell.

41. The method of claim 21, wherein the vector also comprises a promoter inducible in the plant.

42. The method of claim 30 wherein the vector also comprises a promoter inducible in the plant cell.

43. An expression cassette comprising a promoter inducible in plants and a nucleic acid encoding a molybdenum cofactor sulfurase, wherein said molybdenum cofactor sulfurase has a homology of at least 95% with SEO ID NO: 2.

* * * * *

SEQUENCE LISTING

<160> NUMBER OF SEQ ID NOS: 6

<210> SEQ ID NO 1
<211> LENGTH: 2460
<212> TYPE: DNA
<213> ORGANISM: Arabidopsis sp.

<400> SEQUENCE: 1

```
atggaagcat ttcttaagga attcggagat tattatggat acccagatgg tcccaagaac      60
attcaagaga tccgcgacac cgaattcaag agattagata aagtgttgt atacttggat      120 catgctggtt ctactttgta ttctgagttg cagatggaat atatttttaa ggacttcaca     180
agcaatgttt ttggaaatcc acatagtcaa agtgatatca gttcggccac cagtgacctt     240
atagcggatg ctcgacatca ggtgcttgaa tactttaatg catctcctga agattacagt     300
tgcttattca cctccggagc cacagcagcg ctgaagcttg tcggagagac ttttccgtgg     360
acccaagaca gtaatttttt gtataccatg gagaatcaca acagtgtact tggtattagg     420
gaatatgcat tagctcaagg tgcttcagca tgtgcagtgg atattgaaga ggcagctaac     480
caaccaggcc agcttacaaa ttcaggacca tctatcaagg taaagcatcg tgctgtgcag     540
atgagaaaca cttctaaact ccaaaaggaa gagtcaagag gaaatgccta taatctattt     600
gctttcccct cggagtgcaa tttttctggc ctgaggttta atctagatct ggtgaagttg     660
atgaaagaaa atactgagac cgtgctacaa ggctcccccct ttagcaagag caagcggtgg     720
atggtcttga ttgatgctgc aaagggttgt gctacactac cacctgattt atcggagtat     780
cctgcagatt ttgttgttct gtcattctac aagttatttg gttatcctac tgggcttggc     840
gctctccttg tacggaatga tgcagccaaa ttgctcaaaa agacttattt tagtggaggc     900
actgttgctg cttcaattgc tgacatcgac tttgtaaaaa gaagggaaag ggtggaggag     960
ttttttgagg atggttctgc ttcattcctg agcatagcag ccatccgtca tggcttcaaa    1020
ttactcaagt cgcttacacc ttctgcaatt tggatgcaca caacgtcact ttccatatat    1080
gtgaaaaaga agcttcaggc tttacgacat ggaaacgggg ctgctgtatg tgttctgtat    1140
ggcagtgaaa atctggagtt atcttcacat aaatcaggcc caacggttac attcaacttg    1200
aaaagacctg atggctcttg gtttggctac ttggaggtgg agaagcttgc ttctttatct    1260
ggaattcagt tacggacagg atgtttttgc aatcctggcg catgtgcaaa gtatctcgag    1320
ttatcccatt ctgagctacg gtctaatgta gaggctgggc atatttgctg ggatgacaat    1380
gatgtgataa atggaaaacc aacagggct gttagggttt cgtttggtta tatgtcaacc    1440
tttgaagatg ccaagaaatt tattgatttc atcataagtt catttgcttc acctccaaag    1500
aagactggga atggaaccgt cgtcagtgga aggtttcctc aactctctag tgaagacctt    1560
```

-continued

```
gaaagtaaag aatctttcc aagccactac cttaagtcaa ttactgtata cccgatcaag    1620
tcatgtgctg gattttctgt gatacgttgg ccactttgca aacaggcct gctgcatgat    1680 cgagaatgga tggttcaggg tctgaccggt gaaattctta cccaaaagaa ggtgcctgag   1740
atgtctctta taaaaacctt tatcgacctt gaggaaggac tactgtctgt agaatcttct   1800
cgctgcgaag acaagttgca catcagaatc aagtctgatt catataaccc gaggaacgat   1860
gagtttgatt cacatgccaa catacttgaa accgtaatg aggaaactag aatcaatcgt    1920
tggttcacca atgccattgg tcgacaatgc aagttgctac ggtattctag ctctacttcc   1980
aaagactgct tgaacagaaa caagagtcct ggtttgtgca gagatttgga agcaatatc    2040 aactttgcta atgaagctca gttcttgtta atctccgagg agagtgttgc tgacctaaac   2100
agaagattag aagcaaaaga cgaggattac aaacgggctc atgaaaaact caatccacat   2160
aggttcagac caaatctggt tatatctgga ggtgaaccat acggggaaga taaatggaaa   2220
actgtcaaga taggagacaa tcatttcaca tcattgggcg ttgtaaccg gtgccagatg    2280 ataaacataa gtaatgaagc tggactagtg aagaaatcca atgagcctt aacaactta    2340 gcttcatata ggagagtaaa gggaaagatc ttgtttggaa cgcttttgag atacgagatt   2400
gatgagaaaa gacaatgttg gattggagtt ggggaagaag ttaatccaga tattgaataa   2460
```

<210> SEQ ID NO 2
<211> LENGTH: 819
<212> TYPE: PRT
<213> ORGANISM: Arabidopsis sp.

<400> SEQUENCE: 2

```
Met Glu Ala Phe Leu Lys Glu Phe Gly Asp Tyr Tyr Gly Tyr Pro Asp
1               5                   10                  15

Gly Pro Lys Asn Ile Gln Glu Ile Arg Asp Thr Glu Phe Lys Arg Leu
                20                  25                  30

Asp Lys Gly Val Val Tyr Leu Asp His Ala Gly Ser Thr Leu Tyr Ser
            35                  40                  45

Glu Leu Gln Met Glu Tyr Ile Phe Lys Asp Phe Thr Ser Asn Val Phe
        50                  55                  60

Gly Asn Pro His Ser Gln Ser Asp Ile Ser Ala Thr Ser Asp Leu
65                  70                  75                  80

Ile Ala Asp Ala Arg His Gln Val Leu Glu Tyr Phe Asn Ala Ser Pro
                85                  90                  95

Glu Asp Tyr Ser Cys Leu Phe Thr Ser Gly Ala Thr Ala Ala Leu Lys
            100                 105                 110

Leu Val Gly Glu Thr Phe Pro Trp Thr Gln Asp Ser Asn Phe Leu Tyr
        115                 120                 125

Thr Met Glu Asn His Asn Ser Val Leu Gly Ile Arg Glu Tyr Ala Leu
    130                 135                 140

Ala Gln Gly Ala Ser Ala Cys Ala Val Asp Ile Glu Glu Ala Ala Asn
145                 150                 155                 160

Gln Pro Gly Gln Leu Thr Asn Ser Gly Pro Ser Ile Lys Val Lys His
                165                 170                 175

Arg Ala Val Gln Met Arg Asn Thr Ser Lys Leu Gln Lys Glu Glu Ser
            180                 185                 190

Arg Gly Asn Ala Tyr Asn Leu Phe Ala Phe Pro Ser Glu Cys Asn Phe
        195                 200                 205

Ser Gly Leu Arg Phe Asn Leu Asp Leu Val Lys Leu Met Lys Glu Asn
    210                 215                 220
```

-continued

```
Thr Glu Thr Val Leu Gln Gly Ser Pro Phe Ser Lys Ser Lys Arg Trp
225                 230                 235                 240

Met Val Leu Ile Asp Ala Ala Lys Gly Cys Ala Thr Leu Pro Pro Asp
            245                 250                 255

Leu Ser Glu Tyr Pro Ala Asp Phe Val Val Leu Ser Phe Tyr Lys Leu
        260                 265                 270

Phe Gly Tyr Pro Thr Gly Leu Gly Ala Leu Leu Val Arg Asn Asp Ala
    275                 280                 285

Ala Lys Leu Leu Lys Lys Thr Tyr Phe Ser Gly Thr Val Ala Ala
290                 295                 300

Ser Ile Ala Asp Ile Asp Phe Val Lys Arg Arg Glu Arg Val Glu Glu
305                 310                 315                 320

Phe Phe Glu Asp Gly Ser Ala Ser Phe Leu Ser Ile Ala Ala Ile Arg
                325                 330                 335

His Gly Phe Lys Leu Leu Lys Ser Leu Thr Pro Ser Ala Ile Trp Met
            340                 345                 350

His Thr Thr Ser Leu Ser Ile Tyr Val Lys Lys Leu Gln Ala Leu
            355                 360                 365

Arg His Gly Asn Gly Ala Ala Val Cys Val Leu Tyr Gly Ser Glu Asn
        370                 375                 380

Leu Glu Leu Ser Ser His Lys Ser Gly Pro Thr Val Thr Phe Asn Leu
385                 390                 395                 400

Lys Arg Pro Asp Gly Ser Trp Phe Gly Tyr Leu Glu Val Glu Lys Leu
                405                 410                 415

Ala Ser Leu Ser Gly Ile Gln Leu Arg Thr Gly Cys Phe Cys Asn Pro
            420                 425                 430

Gly Ala Cys Ala Lys Tyr Leu Glu Leu Ser His Ser Glu Leu Arg Ser
        435                 440                 445

Asn Val Glu Ala Gly His Ile Cys Trp Asp Asp Asn Asp Val Ile Asn
450                 455                 460

Gly Lys Pro Thr Gly Ala Val Arg Val Ser Phe Gly Tyr Met Ser Thr
465                 470                 475                 480

Phe Glu Asp Ala Lys Lys Phe Ile Asp Phe Ile Ser Ser Phe Ala
                485                 490                 495

Ser Pro Pro Lys Lys Thr Gly Asn Gly Thr Val Val Ser Gly Arg Phe
            500                 505                 510

Pro Gln Leu Pro Ser Glu Asp Leu Glu Ser Lys Glu Ser Phe Pro Ser
        515                 520                 525

His Tyr Leu Lys Ser Ile Thr Val Tyr Pro Ile Lys Ser Cys Ala Gly
    530                 535                 540

Phe Ser Val Ile Arg Trp Pro Leu Cys Arg Thr Gly Leu Leu His Asp
545                 550                 555                 560

Arg Glu Trp Met Val Gln Gly Leu Thr Gly Glu Ile Leu Thr Gln Lys
                565                 570                 575

Lys Val Pro Glu Met Ser Leu Ile Lys Thr Phe Ile Asp Leu Glu Glu
            580                 585                 590

Gly Leu Leu Ser Val Glu Ser Ser Arg Cys Glu Asp Lys Leu His Ile
        595                 600                 605

Arg Ile Lys Ser Asp Ser Tyr Asn Pro Arg Asn Asp Glu Phe Asp Ser
    610                 615                 620

His Ala Asn Ile Leu Glu Asn Arg Asn Glu Glu Thr Arg Ile Asn Arg
625                 630                 635                 640
```

```
Trp Phe Thr Asn Ala Ile Gly Arg Gln Cys Lys Leu Leu Arg Tyr Ser
            645                 650                 655

Ser Ser Thr Ser Lys Asp Cys Leu Asn Arg Asn Lys Ser Pro Gly Leu
            660                 665                 670

Cys Arg Asp Leu Glu Ser Asn Ile Asn Phe Ala Asn Glu Ala Gln Phe
            675                 680                 685

Leu Leu Ile Ser Glu Glu Ser Val Ala Asp Leu Asn Arg Arg Leu Glu
            690                 695                 700

Ala Lys Asp Glu Asp Tyr Lys Arg Ala His Glu Lys Leu Asn Pro His
705                 710                 715                 720

Arg Phe Arg Pro Asn Leu Val Ile Ser Gly Glu Pro Tyr Gly Glu
                725                 730                 735

Asp Lys Trp Lys Thr Val Lys Ile Gly Asp Asn His Phe Thr Ser Leu
            740                 745                 750

Gly Gly Cys Asn Arg Cys Gln Met Ile Asn Ile Ser Asn Glu Ala Gly
            755                 760                 765

Leu Val Lys Lys Ser Asn Glu Pro Leu Thr Thr Leu Ala Ser Tyr Arg
            770                 775                 780

Arg Val Lys Gly Lys Ile Leu Phe Gly Thr Leu Leu Arg Tyr Glu Ile
785                 790                 795                 800

Asp Glu Lys Arg Gln Cys Trp Ile Gly Val Gly Glu Val Asn Pro
                805                 810                 815

Asp Ile Glu

<210> SEQ ID NO 3
<211> LENGTH: 888
<212> TYPE: PRT
<213> ORGANISM: Homo sapiens

<400> SEQUENCE: 3

Met Ala Gly Ala Ala Glu Ser Gly Arg Glu Leu Trp Thr Phe Ala
1               5                   10                  15

Gly Ser Arg Asp Pro Ser Ala Pro Arg Leu Ala Tyr Gly Tyr Gly Pro
            20                  25                  30

Gly Ser Leu Arg Glu Leu Arg Ala Arg Glu Phe Ser Arg Leu Ala Gly
        35                  40                  45

Thr Val Tyr Leu Asp His Ala Gly Ala Thr Leu Phe Ser Gln Ser Gln
    50                  55                  60

Leu Glu Ser Phe Thr Ser Asp Leu Met Glu Asn Thr Tyr Gly Asn Pro
65                  70                  75                  80

His Ser Gln Asn Ile Ser Ser Lys Leu Thr His Asp Thr Val Glu Gln
                85                  90                  95

Val Arg Tyr Arg Ile Leu Ala His Phe His Thr Thr Ala Glu Asp Tyr
            100                 105                 110

Thr Val Ile Phe Thr Ala Gly Ser Thr Ala Ala Leu Lys Leu Val Ala
            115                 120                 125

Glu Ala Phe Pro Trp Val Ser Gln Gly Pro Glu Ser Ser Gly Ser Arg
        130                 135                 140

Phe Cys Tyr Leu Thr Asp Ser His Thr Ser Val Val Gly Met Arg Asn
145                 150                 155                 160

Val Thr Met Ala Ile Asn Val Ile Ser Ile Pro Val Arg Pro Glu Asp
                165                 170                 175

Leu Trp Ser Ala Glu Glu Arg Gly Ala Ser Ala Ser Asn Pro Asp Cys
            180                 185                 190
```

```
Gln Leu Pro His Leu Phe Cys Tyr Pro Ala Gln Ser Asn Phe Ser Gly
        195                 200                 205

Val Arg Tyr Pro Leu Ser Trp Ile Glu Glu Val Lys Ser Gly Arg Leu
    210                 215                 220

Arg Pro Val Ser Thr Pro Gly Lys Trp Phe Val Leu Leu Asp Ala Ala
225                 230                 235                 240

Ser Tyr Val Ser Thr Ser Pro Leu Asp Leu Ser Ala His Gln Ala Asp
                245                 250                 255

Phe Val Pro Ile Ser Phe Tyr Lys Ile Phe Gly Phe Pro Thr Gly Leu
            260                 265                 270

Gly Ala Leu Leu Val His Asn Arg Ala Pro Leu Leu Arg Lys Thr
        275                 280                 285

Tyr Phe Gly Gly Thr Ala Ser Ala Tyr Leu Ala Gly Glu Asp Phe
        290                 295                 300

Tyr Ile Pro Arg Gln Ser Val Ala Gln Arg Phe Glu Asp Gly Thr Ile
305                 310                 315                 320

Ser Phe Leu Asp Val Ile Ala Leu Lys His Gly Phe Asp Thr Leu Glu
                325                 330                 335

Arg Leu Thr Gly Gly Met Glu Asn Ile Lys Gln His Thr Phe Thr Leu
                340                 345                 350

Ala Gln Tyr Thr Tyr Met Ala Leu Ser Ser Leu Gln Tyr Pro Asn Gly
        355                 360                 365

Ala Pro Val Val Arg Ile Tyr Ser Asp Ser Glu Phe Ser Pro Glu
        370                 375                 380

Val Gln Gly Pro Ile Ile Asn Phe Asn Val Leu Asp Asp Lys Gly Asn
385                 390                 395                 400

Ile Ile Gly Tyr Ser Gln Val Asp Lys Met Ala Ser Leu Tyr Asn Ile
                405                 410                 415

His Leu Arg Thr Gly Cys Phe Cys Asn Thr Gly Ala Cys Gln Arg His
                420                 425                 430

Leu Gly Ile Ser Asn Glu Met Val Arg Lys His Phe Gln Ala Gly His
        435                 440                 445

Val Cys Gly Asp Asn Met Asp Leu Ile Asp Gly Gln Pro Thr Gly Ser
    450                 455                 460

Val Arg Ile Ser Phe Gly Tyr Met Ser Thr Leu Asp Asp Val Gln Ala
465                 470                 475                 480

Phe Leu Arg Phe Ile Ile Asp Thr Arg Leu His Ser Ser Gly Asp Trp
            485                 490                 495

Pro Val Pro Gln Ala His Ala Asp Thr Gly Glu Thr Gly Ala Pro Ser
                500                 505                 510

Ala Asp Ser Gln Ala Asp Val Ile Pro Ala Val Met Gly Arg Arg Ser
        515                 520                 525

Leu Ser Pro Gln Glu Asp Ala Leu Thr Gly Ser Arg Val Trp Asn Asn
    530                 535                 540

Ser Ser Thr Val Asn Ala Val Pro Val Ala Pro Val Cys Asp Val
545                 550                 555                 560

Ala Arg Thr Gln Pro Thr Pro Ser Glu Lys Ala Ala Gly Val Leu Glu
                565                 570                 575

Gly Ala Leu Gly Pro His Val Val Thr Asn Leu Tyr Leu Tyr Pro Ile
        580                 585                 590

Lys Ser Cys Ala Ala Phe Glu Val Thr Arg Trp Pro Val Gly Asn Gln
            595                 600                 605

Gly Leu Leu Tyr Asp Arg Ser Trp Met Val Val Asn His Asn Gly Val
```

```
                        610                 615                 620
Cys Leu Ser Gln Lys Gln Glu Pro Arg Leu Cys Leu Ile Gln Pro Phe
625                 630                 635                 640

Ile Asp Leu Arg Gln Arg Ile Met Val Ile Lys Ala Lys Gly Met Glu
                645                 650                 655

Pro Ile Glu Val Pro Leu Glu Glu Asn Ser Glu Arg Thr Gln Ile Arg
            660                 665                 670

Gln Ser Arg Val Cys Ala Asp Arg Val Ser Thr Tyr Asp Cys Gly Glu
        675                 680                 685

Lys Ile Ser Ser Trp Leu Ser Thr Phe Phe Gly Arg Pro Cys Asn Leu
690                 695                 700

Ile Lys Gln Ser Ser Asn Ser Gln Arg Asn Ala Lys Lys His Gly
705                 710                 715                 720

Lys Asp Gln Leu Pro Gly Thr Met Ala Thr Leu Ser Leu Val Asn Glu
                725                 730                 735

Ala Gln Tyr Leu Leu Ile Asn Thr Ser Ser Ile Leu Glu Leu His Arg
            740                 745                 750

Gln Leu Asn Thr Ser Asp Glu Asn Gly Lys Glu Leu Phe Ser Leu
        755                 760                 765

Lys Asp Leu Ser Leu Arg Phe Arg Ala Asn Ile Ile Asn Gly Lys
770                 775                 780

Arg Ala Phe Glu Glu Glu Lys Trp Asp Glu Ile Ser Ile Gly Ser Leu
785                 790                 795                 800

Arg Phe Gln Val Leu Gly Pro Cys His Arg Cys Gln Met Ile Cys Ile
                805                 810                 815

Asp Gln Gln Thr Gly Gln Arg Asn Gln His Val Phe Gln Lys Leu Ser
            820                 825                 830

Glu Ser Arg Glu Thr Lys Val Asn Phe Gly Met Tyr Leu Met His Ala
        835                 840                 845

Ser Leu Asp Leu Ser Ser Pro Cys Phe Leu Ser Val Gly Ser Gln Val
    850                 855                 860

Leu Pro Val Leu Lys Glu Asn Val Glu Gly His Asp Leu Pro Ala Ser
865                 870                 875                 880

Glu Lys His Gln Asp Val Thr Ser
                885

<210> SEQ ID NO 4
<211> LENGTH: 849
<212> TYPE: PRT
<213> ORGANISM: Bos Taurus

<400> SEQUENCE: 4

Met Gln Ser Arg Gln Pro Arg Ala Leu Leu Pro Arg Ser Pro Gly Thr
1               5                   10                  15

Val Tyr Leu Asp His Ala Gly Thr Thr Leu Phe Pro Gln Ser Gln Ile
                20                  25                  30

Thr Ser Phe Met Lys Asp Leu Met Glu Asn Val Tyr Gly Asn Pro His
            35                  40                  45

Ser Gln Asn Ile Ser Ser Lys Leu Thr His Asp Thr Val Glu Gln Val
        50                  55                  60

Arg Phe Arg Ile Leu Ala His Phe His Thr Ser Pro Glu Asp Tyr Thr
65                  70                  75                  80

Val Ile Phe Thr Ser Gly Ser Thr Ala Ala Leu Lys Leu Val Ala Glu
                85                  90                  95
```

```
Ala Phe Pro Trp Val Ser Pro Gly Glu Gly Ser Gly Cys Phe
                100             105             110
Cys Tyr Leu Thr Asp Ser His Thr Ser Val Val Gly Met Arg Lys Ile
            115                 120                 125
Thr Ala Ala Met Asn Val Ser Ser Ile Pro Val Arg Pro Glu Asp Met
        130                 135                 140
Trp Ser Ala Glu Arg Gln Asp Ala Ala Ala Gly Asp Pro Ala Gly
145                 150                 155                 160
Gln Pro Pro His Leu Phe Cys Tyr Pro Ala Gln Ser Asn Phe Ser Gly
                165                 170                 175
Thr Arg Tyr Pro Leu Ser Trp Ile Gly Glu Val Lys Ser Gly Arg Arg
            180                 185                 190
Arg Pro Ala Ser Arg Pro Gly Lys Trp Phe Val Leu Leu Asp Ala Ala
        195                 200                 205
Ala Phe Val Gly Thr Ser Pro Leu Asp Leu Ser Val His Gln Ala Asp
    210                 215                 220
Phe Val Pro Ile Ser Phe Tyr Lys Ile Phe Gly Phe Pro Thr Gly Leu
225                 230                 235                 240
Gly Ala Leu Leu Val Asn Asn Arg Leu Ala Ala Leu Leu Arg Lys Thr
                245                 250                 255
Tyr Phe Gly Gly Gly Thr Ala Ala Ala Tyr Leu Ala Gly Asp Asp Phe
            260                 265                 270
Tyr Val Pro Arg Glu Ser Val Ala Glu Arg Phe Glu Asp Gly Thr Ile
        275                 280                 285
Ser Phe Leu Asp Val Ile Ala Leu Lys His Gly Phe Asp Ala Leu Glu
    290                 295                 300
Arg Leu Thr Gly Gly Met Glu Ser Ile Arg Gln His Thr Phe Thr Leu
305                 310                 315                 320
Ala Gln Tyr Thr Tyr Thr Ala Leu Ser Ser Leu Arg Tyr Pro Asn Gly
                325                 330                 335
Ala Pro Val Val Gln Ile Tyr Ser Asp Ser Asp Phe Ser Ser Pro Glu
            340                 345                 350
Val Gln Gly Pro Val Ile Ser Phe Asn Val Leu Asp Asp His Gly Asn
        355                 360                 365
Val Val Gly Tyr Ser Gln Val Asp Lys Met Ala Ser Leu His Asn Ile
    370                 375                 380
His Val Arg Thr Gly Cys Phe Cys Asn Thr Gly Ala Cys Gln Arg His
385                 390                 395                 400
Leu Gly Ile Ser Asp Glu Met Val Lys Lys His Leu Gln Ala Gly His
                405                 410                 415
Val Cys Gly Asp Asp Val Asp Leu Ile Asp Gly Gln Pro Thr Gly Ser
            420                 425                 430
Val Arg Ile Ser Phe Gly Tyr Met Ser Thr Leu Glu Asp Ala Gln Ala
        435                 440                 445
Phe Leu Arg Phe Ile Ile Ala Thr Arg Leu His Ser Ser His Gly Gln
    450                 455                 460
Pro Leu Pro Leu Ala Thr Pro Gly Glu Ala Gly Ala Pro Pro Glu Asp
465                 470                 475                 480
Ser Glu Ala Gln Asn Ala Met Pro Ala Ala Arg Ala Arg Gly Ser Ser
                485                 490                 495
Ser Pro Gln Glu Asp Thr Ser Pro His Ser Gly Val Trp Asn Asn Ser
            500                 505                 510
Pro Thr Ala Val Asp Ala Glu Gly Leu Cys Pro Pro Leu Leu Glu Ala
```

```
                515                 520                 525
Thr Gly Thr Gln Gln Thr Thr Ser Glu Lys Ala Ala Asp Val Pro Asp
            530                 535                 540

Gly Asp Leu Arg Ser His Val Ile Thr Asn Leu Phe Leu Tyr Pro Ile
545                 550                 555                 560

Lys Ser Cys Ala Ala Phe Glu Val Ile Arg Trp Pro Leu Gly Ser Gln
                565                 570                 575

Gly Leu Leu Tyr Asp Arg Ser Trp Met Val Asn His Asn Gly Ile
                580                 585                 590

Cys Leu Ser Gln Lys Gln Glu Pro Arg Leu Cys Leu Ile Gln Pro Phe
            595                 600                 605

Ile Asp Leu Gln Arg Arg Ile Met Val Ile Lys Ala Gln Gly Met Glu
            610                 615                 620

Pro Ile Glu Val Pro Leu Glu Asn Ser Glu Gln Val Gln Ile Cys
625                 630                 635                 640

Gln Ser Lys Val Cys Ala Asp Arg Val Asn Thr Tyr Asp Cys Gly Glu
                645                 650                 655

Lys Ile Ser Asn Trp Leu Ser Lys Phe Phe Gly Arg Pro Tyr His Leu
                660                 665                 670

Ile Lys Gln Ser Ser Asp Phe Gln Arg Asn Ala Lys Lys His Gly
            675                 680                 685

Lys Asp Gln Ser Ala His Thr Thr Ala Thr Leu Ser Leu Val Asn Glu
690                 695                 700

Ala Gln Tyr Leu Leu Ile Asn Arg Ser Ser Ile Leu Glu Leu Gln Gln
705                 710                 715                 720

Gln Leu Ser Thr Ser Cys Glu Asn Gly Lys Glu Glu Leu Phe Pro Met
            725                 730                 735

Asn Asn Leu Ile Ser Arg Phe Arg Ala Asn Ile Ile Thr Asn Gly Thr
            740                 745                 750

Arg Ala Phe Glu Glu Lys Trp Asp Glu Ile Ser Ile Gly Ser Leu
            755                 760                 765

Arg Phe Gln Val Leu Gly Pro Cys His Arg Cys Gln Met Ile Cys Ile
770                 775                 780

Asp Gln Gln Thr Gly Gln Arg Asn Gln Asp Val Phe Gln Lys Leu Ser
785                 790                 795                 800

Glu Arg Arg Glu Arg Lys Val Lys Phe Gly Val Tyr Leu Met His Thr
                805                 810                 815

Ser Leu Asp Leu Ser Ser Pro Cys Tyr Leu Ser Val Gly Ser Gln Val
            820                 825                 830

Leu Pro Leu Leu Lys Glu Asn Met Glu His His Asp Ile Pro Ala Thr
            835                 840                 845

Glu

<210> SEQ ID NO 5
<211> LENGTH: 781
<212> TYPE: PRT
<213> ORGANISM: Drosophila melanogaster

<400> SEQUENCE: 5

Met Thr Ser Tyr Arg Pro Glu Phe Ser Ala Ser Glu Gln Ser Gln Ile
1               5                   10                  15

Asp Ala Glu Phe Ser Arg Leu Ala Ser Asn Lys Ser Val Tyr Leu Asp
                20                  25                  30

His Ala Gly Thr Thr Leu Tyr Ala Glu Ser Gln Val Thr Ala Ala Ala
```

-continued

```
                35                  40                  45
Glu Gln Leu Gln Arg Asn Val Ile Cys Asn Pro His Thr Cys Arg Leu
 50                  55                  60

Thr Gly Asp Phe Val Asp Gln Val Arg Phe Lys Ile Leu Glu Phe Phe
 65                  70                  75                  80

Asn Thr Thr Ala Glu Asp Tyr His Val Ile Phe Thr Ala Asn Ala Thr
                 85                  90                  95

Ala Ala Leu Ser Leu Val Ala Glu Asn Phe Asp Phe Gly Ser Ser Gly
                100                 105                 110

Glu Phe His Phe Cys Gln Glu Asn His Thr Ser Val Leu Gly Met Arg
                115                 120                 125

Glu Arg Val Arg Glu Asn Gly Ile Tyr Met Leu Arg Glu Asn Glu Ile
130                 135                 140

Ser Gly Gly Lys His Lys Ala Asn Gly Lys Val His Glu Val Ser Gly
145                 150                 155                 160

Lys Thr Gly Asn Ser Leu Leu Thr Phe Ser Ala Gln Cys Asn Phe Ser
                165                 170                 175

Gly Tyr Lys Ile Pro Leu Glu Val Ile Glu Gln Ile Gln Ile Asp Gly
                180                 185                 190

Leu Ala Lys Pro Gly Lys Glu Leu Trp Ser Ser Leu Gly Glu Lys Lys
                195                 200                 205

Lys Asn Met His Asn Asp Tyr Tyr Ile Cys Leu Asp Ala Ala Ser Phe
210                 215                 220

Val Ala Thr Ser Pro Leu Asp Leu Gln Lys Tyr Arg Pro Asp Tyr Val
225                 230                 235                 240

Cys Leu Ser Phe Tyr Lys Ile Phe Gly Tyr Pro Thr Gly Val Gly Ala
                245                 250                 255

Leu Leu Val Ser Arg Arg Gly Ala Glu Val Phe Gln Lys Arg Arg Phe
                260                 265                 270

Phe Gly Gly Gly Thr Ile Asn Tyr Ala Tyr Pro His Ala Met Asp Tyr
                275                 280                 285

Gln Leu Arg Glu Thr Phe His Gln Arg Tyr Glu Asp Gly Thr Leu Pro
290                 295                 300

Phe Leu Ser Ile Val Gly Leu Leu Glu Gly Phe Arg Thr Leu Glu Arg
305                 310                 315                 320

Leu Val Pro Arg Thr Asp Glu Phe Ser Thr Met Glu Arg Ile Ser Arg
                325                 330                 335

His Val Phe Gly Leu Ala Lys Tyr Leu Glu Asp Gln Leu Arg Gln Leu
                340                 345                 350

His His Pro Asn Gly Glu Pro Leu Val Lys Leu Tyr Asn Lys Val Gly
                355                 360                 365

Tyr Gln Asp Lys Ser Arg Gln Gly Gly Ile Val Ala Phe Asn Val Arg
370                 375                 380

Thr Glu Ser Gly Ser Phe Val Gly Phe Gly Glu Ile Ala Cys Val Ala
385                 390                 395                 400

Ala Leu His Gly Ile Leu Leu Arg Thr Gly Cys Phe Cys Asn Ile Gly
                405                 410                 415

Ala Cys Gln Tyr Tyr Leu Gly Leu Asp Glu Asp Ala Leu Asp Ala Ile
                420                 425                 430

Tyr Lys Arg Ala Gly Arg Ile Cys Gly Asp Tyr Phe Asp Leu Ile Asp
                435                 440                 445

Gly Gln Pro Thr Gly Ala Val Arg Val Ser Phe Gly Tyr Met Thr Thr
450                 455                 460
```

-continued

```
Ile Gln Asp Val Asp Lys Leu Leu Gln Met Leu Arg Ser Ser Tyr Leu
465                 470                 475                 480

Ala Thr Lys Pro Leu Gln Arg Ile Gln Phe Ile Glu Glu Gln Ala Glu
                485                 490                 495

Gln Leu Pro Pro Leu Leu Lys Glu Arg Val Gln Leu Leu Arg Pro Lys
            500                 505                 510

Leu Leu Gln Met Ala Ile Tyr Pro Val Lys Ser Cys Ala Ala Phe Lys
        515                 520                 525

Ile Glu Leu Pro Gly Ser Trp Pro Leu Thr Asp Gln Gly Leu Lys Tyr
    530                 535                 540

Asp Arg Glu Trp Met Ile Val Asp Met Asn Gly Met Ala Leu Thr Gln
545                 550                 555                 560

Lys Arg Cys Thr Glu Leu Cys Leu Ile Arg Pro Val Ile Lys Val Asp
                565                 570                 575

Gln Leu Glu Leu Gln Phe Gly Glu Asn Ser Thr Ile Ser Val Pro Leu
            580                 585                 590

Ser Leu Asp Asp Gln Ala Ala Asp Thr Ala Lys Cys Val Ser Lys Val
        595                 600                 605

Cys Arg Gln Pro Val Glu Gly Leu Asp Cys Gly Asp Arg Val Ala Gln
    610                 615                 620

Trp Leu Ser Glu Asn Leu Gly Met Glu Gly Leu Arg Leu Leu Arg Gln
625                 630                 635                 640

Ser Gly Gln Arg Asn Ser Ser Lys Asp Gln Gln Lys Leu Ser Leu Val
                645                 650                 655

Asn Gln Ala Gln Phe Leu Leu Leu Asn Lys Ser Ser Val Arg Ser Leu
            660                 665                 670

Gln Phe Glu Glu Pro Leu Asp Glu Thr Val Asp Arg Phe Arg Ala Asn
        675                 680                 685

Ile Ile Ile Asp Thr Gly Ser Ala Phe Glu Glu Leu Thr Tyr Lys Ala
    690                 695                 700

Leu Ser Ile Gly Gly Ile Gln Phe Gln Val Glu Gly Pro Cys Gln Arg
705                 710                 715                 720

Cys Asp Met Ile Cys Ile Asn Gln Arg Thr Gly Glu Arg Ser Pro Glu
                725                 730                 735

Thr Leu Thr Thr Ile Ser Arg Leu Gln Lys Gly Arg Met Arg Phe Gly
            740                 745                 750

Ile Tyr Ile Thr Arg Ile Pro Gln Asp Thr Lys Glu Leu Glu Pro Lys
        755                 760                 765

Glu Gln His Met Thr Cys Gly Asp Val Val Leu Val Glu
    770                 775                 780
```

<210> SEQ ID NO 6
<211> LENGTH: 839
<212> TYPE: PRT
<213> ORGANISM: Aspergillus nidulans

<400> SEQUENCE: 6

```
Met Asn Leu Ser Lys Gly Thr Ala Ala Ala Tyr Cys Ser Gly Tyr Ser
1               5                   10                  15

Glu Asp Val Asp Val Ile Arg Glu Arg Glu Tyr Pro Leu Leu Lys Asp
                20                  25                  30

Thr Thr Tyr Leu Asp His Ala Gly Thr Thr Leu Tyr Ala Asn Ser Leu
            35                  40                  45

Ile His Ser Phe Gly Arg Asp Leu Thr Gly Asn Leu Tyr Gly Asn Pro
```

-continued

```
                50                  55                  60
His Ser Met Ser Ala Ser Ser Gln Leu Ser Ala Gln Arg Ala Gly Arg
 65                  70                  75                  80

Tyr Ser Leu Arg Ala Leu Arg Phe Phe Asn Ala Asp Pro Asp Glu Phe
                     85                  90                  95

Asp Leu Val Phe Val Ala Asn Ala Thr Ala Gly Ile Lys Leu Val Ala
                    100                 105                 110

Asp Ala Leu Gln Asn Ser Pro Gln Gly Phe Trp Tyr Gly Tyr Tyr Val
                    115                 120                 125

Asp Ala His Thr Ser Leu Val Gly Val Arg Glu Leu Ala Lys Met Gly
130                 135                 140

Ser Arg Cys Phe Val Asn Glu Asp Glu Val Asp Ser Trp Ile Ser Gly
145                 150                 155                 160

Leu Gly Ser Arg Arg Glu Glu Ser Leu Gly Leu Phe Ala Tyr Pro Ala
                    165                 170                 175

Gln Ser Asn Met Asn Gly Arg Arg Val Pro Met Arg Trp Cys Glu Gln
                    180                 185                 190

Ile Arg Ala Gln Lys Glu Asn Ala Asp Asn Met Ile Tyr Thr Leu Leu
                    195                 200                 205

Asp Ala Ala Ser Phe Val Ser Thr Ser Pro Leu Asp Leu Ser Lys Ile
                    210                 215                 220

Ala Ala Ala Pro Asp Phe Thr Val Leu Ser Phe Tyr Lys Ile Phe Gly
225                 230                 235                 240

Phe Pro Asp Leu Gly Ala Leu Ile Val Arg Lys Ser Ser Gly Asp Val
                    245                 250                 255

Phe Lys His Arg Lys Phe Phe Gly Gly Gly Thr Val Asp Met Val Leu
                    260                 265                 270

Thr Asp Gly Asn Pro Trp His Ala Lys Lys Gln Ser Ser Ile His Gln
                    275                 280                 285

Ser Leu Glu Asp Gly Thr Leu Pro Phe His Ser Ile Ile Ala Leu Asp
                    290                 295                 300

Ser Ala Phe Glu Thr His Gly Arg Leu Phe Arg Ser Met Glu Asn Val
305                 310                 315                 320

Ala Ser His Thr Arg Phe Leu Ala Lys Arg Leu Arg Asp Arg Met Asn
                    325                 330                 335

Ala Leu Lys His Tyr Asn Gly Ser Lys Val Cys Gln Leu Tyr Met Ser
                    340                 345                 350

Pro Asn Ser Ser Tyr Asp Ala Ser Ser Gln Gly Pro Ile Leu Ala
                    355                 360                 365

Phe Asn Leu Arg Asn Ser Arg Gly Met Trp Ile Gly Lys Ser Glu Val
                    370                 375                 380

Glu Arg Leu Ala Ser Ile Lys Asn Ile Gln Ile Arg Ser Gly Thr Leu
385                 390                 395                 400

Cys Asn Pro Gly Gly Thr Ala Leu Ser Leu Gly Trp Thr Gly Ala Asp
                    405                 410                 415

Met Leu Arg His Phe Ser Ala Gly Met Arg Cys Gly Asp Asp His Asp
                    420                 425                 430

Ile Met Asp Glu Arg Pro Thr Gly Ile Leu Arg Ile Ser Leu Gly Ala
                    435                 440                 445

Met Ser Ser Leu Thr Asp Val Asp Thr Phe Ile Ala Phe Leu Glu Glu
                    450                 455                 460

Phe Tyr Val Asp Lys Pro Pro Glu Gly Leu Pro Val Pro Leu Thr Gly
465                 470                 475                 480
```

```
Asn Val Ser Leu His Gln Pro Ser Phe Tyr Val Glu Ser Leu Ser Val
                485                 490                 495

Tyr Pro Ile Lys Ser Cys Gly Ala Phe Arg Ile Pro Asp Gly Gln Arg
                500                 505                 510

Trp Glu Val Arg Arg Glu Gly Leu Ala Trp Asp Arg Glu Trp Cys Leu
                515                 520                 525

Val His Gln Gly Thr Gly Ile Thr Leu Asn Gln Lys Arg Tyr Pro Arg
                530                 535                 540

Met Ala Leu Ile Arg Pro Thr Leu Asp Leu Glu Arg Cys Leu Leu Arg
545                 550                 555                 560

Ile Thr Cys Gly Glu Ala Asn Ser Arg Asp Gly Lys Thr Leu Glu Ile
                565                 570                 575

Ser Leu Asn Arg Ile Gly Thr Asn Ser Leu Thr Thr Ser Leu Cys Gln
                580                 585                 590

Asn Ala Ser Lys Pro Ser Thr Val Cys Gly Asp Lys Val Val Leu Gln
                595                 600                 605

Ala Tyr Thr Ser Pro Ala Val Ser Arg Phe Pro Thr Asp Phe Leu Gly
                610                 615                 620

Val Pro Cys Thr Leu Ala Arg Phe Pro Pro Gln Ser Ser Thr Arg Phe
625                 630                 635                 640

His Ser Arg Ala Thr Ala Ala Ile Asn Arg Asp Gln Asn Tyr Ser Gln
                645                 650                 655

Lys Gln Ser Pro Ser Met Pro Gly Ser Phe Pro Gln Ala Pro Ser Ser
                660                 665                 670

Pro Asp Pro Tyr Pro Thr Pro Ile Leu Leu Ser Asn Glu Ser Pro Leu
                675                 680                 685

Leu Leu Ile Ser Arg Ser Ser Val Asn Arg Leu Asn Glu Ser Ile Lys
                690                 695                 700

Ser Ala Ser Gln Pro Cys Ser Asn Pro Gly Ser Ala Ala Ser Lys Lys
705                 710                 715                 720

Ala Val Ala Ala Asp Val Phe Arg Ala Asn Val Val Ala Glu Asn
                725                 730                 735

Ile Ser Thr Ala Glu Arg Pro Tyr Ile Glu Asp Thr Trp Ala Ser Leu
                740                 745                 750

Ser Ile Gly Ser Gly Pro Glu Gln Leu Arg Phe Asp Val Leu Gly Ser
                755                 760                 765

Cys Glu Arg Cys Gln Met Val Cys Val Asp Gln Tyr Thr Gly Gln Arg
                770                 775                 780

Gly Asp Glu Pro Tyr Ala Thr Leu Ala Lys Thr Arg Lys Ile Asp Arg
785                 790                 795                 800

Lys Ile Leu Phe Gly Arg His Ile Ser Pro Val Gly Arg Pro Lys Asp
                805                 810                 815

Ala Glu Asn Gly Cys Leu Gly Thr Ile Met Val Gly Asp Ala Val Thr
                820                 825                 830

Pro Ser Tyr Asp Asn Glu Ser
                835
```